(12) United States Patent
Dorsch et al.

(10) Patent No.: US 7,183,277 B2
(45) Date of Patent: Feb. 27, 2007

(54) CARBOXYLIC ACID AMIDES

(75) Inventors: Dieter Dorsch, Ober-Ramstadt (DE); Werner Mederski, Darmstadt (DE); Johannes Gleitz, Darmstadt (DE); Bertram Cezanne, Mörfelden-Walldorf (DE); Christos Tsaklakidis, Weinheim (DE); Christopher Barnes, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 128 days.

(21) Appl. No.: 10/512,478

(22) PCT Filed: Mar. 31, 2003

(86) PCT No.: PCT/EP03/03331

§ 371 (c)(1),
(2), (4) Date: Oct. 26, 2004

(87) PCT Pub. No.: WO03/093235

PCT Pub. Date: Nov. 13, 2003

(65) Prior Publication Data

US 2005/0171154 A1    Aug. 4, 2005

(30) Foreign Application Priority Data

Apr. 27, 2002  (DE) .................. 102 18 974
Aug. 12, 2002  (DE) .................. 102 36 868

(51) Int. Cl.
| A61K 31/5375 | (2006.01) |
| A61K 31/451 | (2006.01) |
| A61K 31/40 | (2006.01) |
| A61K 31/4168 | (2006.01) |
| A61K 31/433 | (2006.01) |
| C07D 211/72 | (2006.01) |
| C07D 207/22 | (2006.01) |

(52) U.S. Cl. .................. 514/231.2; 514/329; 514/424; 514/363; 514/422; 514/392; 546/194; 546/223; 546/112; 544/164; 548/312.7; 548/138; 548/527; 548/315.1

(58) Field of Classification Search ................ 546/194, 546/223, 112; 548/312.7, 138, 527, 315.1, 548/333.1, 543, 559; 544/164
See application file for complete search history.

(56) References Cited

U.S. PATENT DOCUMENTS

2002/0052417 A1    5/2002  Klinger et al.

FOREIGN PATENT DOCUMENTS

| EP | 321368 A1 * | 6/1989 |
| EP | 1162194 | 12/2001 |
| WO | WO 0248099 | 6/2002 |
| WO | WO 02057236 | 7/2002 |

OTHER PUBLICATIONS

CAS abstract included.*

* cited by examiner

*Primary Examiner*—Joseph K. McKane
*Assistant Examiner*—Jason M. Nolan

(57) ABSTRACT

Novel compounds of the formula I

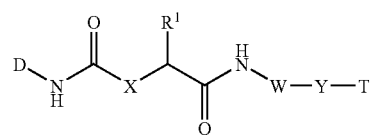

in which
D, W, X, Y, T and $R^1$ are as defined in Patent Claim 1, are inhibitors of coagulation factor Xa and can be employed for the prophylaxis and/or therapy of thromboembolic diseases and for the treatment of tumours.

27 Claims, No Drawings

CARBOXYLIC ACID AMIDES

This application claims priority under 35 U.S.C. §119 of German Application Nos. 10218974.9, filed Apr. 27, 2002, and 10236868.6, filed Aug. 12, 2002.

The invention relates to compounds of the formula I

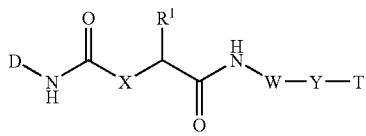

in which
D is phenyl, pyridyl or thienyl, each of which is unsubstituted or monosubstituted or polysubstituted by Hal, A, $OR^2$, $N(R^2)_2$, $NO_2$, CN, $COOR^2$ or $CON(R^2)_2$,
X is $NR^3$ or O,
$R^1$ is H, Ar, Het, cycloalkyl or A, which may be substituted by $OR^2$, $S(O)_mR^2$, $N(R^2)_2$, Ar, Het, cycloalkyl, CN, $COOR^2$ or $CON(R^2)_2$,
$R^2$ is H, A, —[C$(R^3)_2]_n$—Ar, —[C$(R^3)_2]_n$-Het, —[C$(R^3)_2]_n$-cycloalkyl, —[C$(R^3)_2]_n$—N$(R^3)_2$ or —[C$(R^3)_2]_n$—$OR^3$,
$R^3$ is H or A,
W is —[C$(R^3)_2]_n$—,
Y is alkylene, cycloalkylene, Het-diyl or Ar-diyl,
T is a monocyclic or bicyclic saturated, unsaturated or aromatic carbocyclic or heterocyclic ring having from 1 to 4 N, O and/or S atoms, which is monosubstituted or disubstituted by =S, =$NR^2$, =$NOR^2$, =$NCOR^2$, =$NCOOR^2$, =$NOCOR^2$, =N—CN or =N—$NO_2$ and may furthermore be monosubstituted, disubstituted or trisubstituted by Hal, A, —[C$(R^3)_2]_n$—Ar, —[C$(R^3)_2]_n$—Het, —[C$(R^3)_2]_n$-cycloalkyl, $OR^3$, $N(R^3)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_mA$,
A is unbranched or branched alkyl having 1–10 carbon atoms, in which one or two $CH_2$ groups may be replaced by O or S atoms and/or by —CH=CH— groups and/or in addition 1–7 H atoms may be replaced by F,
Ar is phenyl, naphthyl or biphenyl, each of which is unsubstituted or monosubstituted, disubstituted or trisubstituted by Hal, A, $OR^3$, $N(R^3)_2$, $NO_2$, CN, $COOR^3$, $CON(R^3)_2$ $NR^3COA$, $NR^3CON(R^3)_2$, $NR^3SO_2A$, $COR^3$, $SO_2N(R^3)_2$, $S(O)_mA$, —[C$(R^3)_2]_n$—$COOR^{2'}$or —O—[C$(R^3)_2]_o$—$COOR^{2'}$,
$R^{2'}$ is H, A, —[C$(R^3)_2]_n$—Ar', —[C$(R^3)_2]_n$-Het', —[C$(R^3)_2]_n$-cycloalkyl, —[C$(R^3)_2]_n$—$N(R^3)_2$ or —[C$(R^3)_2]_n$—$OR^3$,
$R^{2''}$ is H, A, —[C$(R^3)_2]_n$—Ar', +—[C$(R^3)_2]_n$-cycloalkyl, —[C(R₃)$_2]_n$—$N(R^3)_2$ or —[C$(R^3)_2]_n$—$OR^3$,
Ar' is phenyl or benzyl, each of which is unsubstituted or monosubstituted or disubstituted by Hal or A,
Het is a monocyclic or bicyclic saturated, unsaturated or aromatic heterocyclic ring having from 1 to 4 N, O and/or S atoms, which may be unsubstituted or monosubstituted, disubstituted or trisubstituted by carbonyl oxygen, =S, =$N(R^3)_2$, Hal, A, —[C$(R^3)_2]_n$—Ar, —[C$(R^3)_2]_n$-Het¹, —[C(R₃)$_2]_n$ -cycloalkyl, —[C$(R^3)_2]_n$—$OR^{2'}$, —[C$(R^3)_2]_n$—$N(R^{2'})_2$, $NO_2$, CN, —[C$(R^3)_2]_n$—$COOR^{2'}$, —[C$(R^3)_2]_n$—$CON(R^{2'})_2$, —[C$(R^3)_2]_n$—$NR^{2'}COA$, $NR^{2'}CON(R^{2'})_2$, —[C(R³) $_2]_n$—$NR^{2'}SO_2A$, $COR^{2'}$, $SO_2NR^{2'}$and/or $S(O)_mA$, Het¹ is a monocyclic or bicyclic saturated, unsaturated or aromatic heterocyclic ring having 1 or 2 N, O and/or S atoms, which may be unsubstituted or monosubstituted or disubstituted by carbonyl oxygen, =S, =$N(R^3)_2$, Hal, A, $OR^{2'''}$, $N(R^{2'''})_2$, $NO_2$, CN, $COOR^{2'''}$, $CON(R^{2'''})_2$, $NR^{2'''}COA$, $NR^{2'''}CON(R^{2'''})_2$, $NR^{2'''}SO_2A$, $COR^{2'''}$, $SO_2NR^{2'''}$and/or $S(O)_mA$,
Hal is F, Cl, Br or I,
n is 0, 1 or 2,
m is 0, 1 or 2,
o is 1, 2 or 3, and pharmaceutically usable derivatives, solvates and stereoisomers thereof, including mixtures thereof in all ratios.

The invention had the object of finding novel compounds having valuable properties, in particular those which can be used for the preparation of medicaments.

It has been found that the compounds of the formula I and their salts have very valuable pharmacological properties and are well tolerated. In particular, they exhibit factor Xa-inhibiting properties and can therefore be employed for combating and preventing thromboembolic diseases, such as thrombosis, myocardial infarction, arteriosclerosis, inflammation, apoplexia, angina pectoris, restenosis after angioplasty and claudicatio intermittens.

The compounds of the formula I according to the invention may furthermore be inhibitors of the coagulation factors factor VIIa, factor IXa and thrombin in the blood coagulation cascade.

Aromatic amidine derivatives having an antithrombotic action are disclosed, for example, in EP 0 540 051 B1, WO 98/28269, WO 00/71508, WO 00/71511, WO 00/71493, WO 00/71507, WO 00/71509, WO 00/71512, WO 00/71515 oder WO 00/71516. cyclic guanidines for the treatment of thromboembolic diseases are described, for example, in WO 97/08165. Aromatic heterocyclic compounds having factor Xa-inhibitory activity are disclosed, for example, in WO 96/10022. Substituted N-[(aminoiminomethyl)phenylalkyl] azaheterocyclylamides as factor Xa inhibitors are described in WO 96/40679.

The antithrombotic and anticoagulant effect of the compounds according to the invention is attributed to the inhibitory action against activated coagulation protease, known by the name factor Xa, or to the inhibition of other activated serine proteases, such as factor VIIa, factor IXa or thrombin.

Factor Xa is one of the proteases involved in the complex process of blood coagulation. Factor Xa catalyses the conversion of prothrombin into thrombin. Thrombin cleaves fibrinogen into fibrin monomers, which, after crosslinking, make an elementary contribution to thrombus formation. Activation of thrombin may result in the occurrence of thromboembolic diseases. However, inhibition of thrombin may inhibit the fibrin formation involved in thrombus formation. The inhibition of thrombin can be measured, for example, by the method of G. F. Cousins et al. in *Circulation* 1996, 94, 1705–1712.

Inhibition of factor Xa can thus prevent the formation of thrombin.

The compounds of the formula I according to the invention and their salts engage in the blood coagulation process by inhibiting factor Xa and thus inhibit the formation of thrombuses.

The inhibition of factor Xa by the compounds according to the invention and the measurement of the anticoagulant and antithrombotic activity can be determined by conventional in-vitro or in-vivo methods. A suitable method is described, for example, by J. Hauptmann et al. in *Thrombosis and Haemostasis* 1990, 63, 220–223.

The inhibition of factor Xa can be measured, for example, by the method of T. Hara et al. in *Thromb. Haemostas.* 1994, 71, 314–319.

Coagulation factor VIIa initiates the extrinsic part of the coagulation cascade after binding to tissue factor and contributes to the activation of factor X to give factor Xa. Inhibition of factor VIIa thus prevents the formation of factor Xa and thus subsequent thrombin formation.

The inhibition of factor VIIa by the compounds according to the invention and the measurement of the anticoagulant and antithrombotic activity can be determined by conventional in-vitro or in-vivo methods. A conventional method for the measurement of the inhibition of factor VIIa is described, for example, by H. F. Ronning et al. in *Thrombosis Research* 1996, 84, 73–81.

Coagulation factor IXa is generated in the intrinsic coagulation cascade and is likewise involved in the activation of factor X to give factor Xa. Inhibition of factor IXa can therefore prevent the formation of factor Xa in a different way.

The inhibition of factor IXa by the compounds according to the invention and the measurement of the anticoagulant and antithrombotic activity can be determined by conventional in-vitro or in-vivo methods. A suitable method is described, for example, by J. Chang et al. in *Journal of Biological Chemistry* 1998, 273, 12089–12094.

The compounds according to the invention may furthermore be used for the treatment of tumours, tumour diseases and/or tumour metastases. A correlation between tissue factor TF/factor VIIa and the development of various types of cancer has been indicated by T. Taniguchi and N. R. Lemoine in Biomed. Health Res. (2000), 41 (Molecular Pathogenesis of Pancreatic Cancer), 57–59.

The publications listed below describe an antitumoural action of TF-VII and factor Xa inhibitors for various types of tumour:

K. M. Donnelly et al. in Thromb. Haemost. 1998; 79: 1041–1047;

E. G. Fischer et al. in J. Clin. Invest. 104: 1213–1221 (1999);

B. M. Mueller et al. in J. Clin. Invest. 101: 1372–1378 (1998);

M. E. Bromberg et al. in Thromb. Haemost. 1999; 82: 88–92

The compounds of the formula I can be employed as medicament active ingredients in human and veterinary medicine, in particular for the treatment and prevention of thromboembolic diseases, such as thrombosis, myocardial infarction, arteriosclerosis, inflammation, apoplexia, angina pectoris, restenosis after angioplasty, claudicatio intermittens, venous thrombosis, pulmonary embolism, arterial thrombosis, myocardial ischaemia, unstable angina and strokes based on thrombosis.

The compounds according to the invention are also employed for the treatment or prophylaxis of atherosclerotic diseases, such as coronary arterial disease, cerebral arterial disease or peripheral arterial disease.

The compounds are also employed in combination with other thrombolytic agents in the case of myocardial infarction, furthermore for prophylaxis for reocclusion after thrombolysis, percutaneous transluminal angioplasty (PTCA) and coronary bypass operations.

The compounds according to the invention are furthermore used for the prevention of rethrombosis in microsurgery, furthermore as anticoagulants in connection with artificial organs or in haemodialysis.

The compounds are furthermore used in the cleaning of catheters and medical aids in vivo in patients, or as anticoagulants for the preservation of blood, plasma and other blood products in vitro. The compounds according to the invention are furthermore used for diseases in which blood coagulation makes a crucial contribution to the course of the disease or represents a source of secondary pathology, such as, for example, in cancer, including metastasis, inflammatory disorders, including arthritis, and diabetes.

The compounds according to the invention are furthermore used in the treatment of migraine finden (F. Morales-Asin et al., Headache, 40, 2000, 45–47).

In the treatment of the diseases described, the compounds according to the invention are also employed in combination with other thrombolytically active compounds, such as, for example, with "tissue plasminogen activator" t-PA, modified t-PA, streptokinase or urokinase. The compounds according to the invention are given either at the same time as or before or after the other substances mentioned.

Particular preference is given to simultaneous administration with aspirin in order to prevent recurrence of the clot formation.

The compounds according to the invention are also used in combination with blood platelet glycoprotein receptor (IIb/IIIa) antagonists, which inhibit blood platelet aggregation.

The invention relates to the compounds of the formula I and salts thereof and to a process for the preparation of compounds of the formula I according to claims 1–16 and pharmaceutically usable derivatives, solvates and stereoisomers thereof, characterised in that a) a compound of the formula II

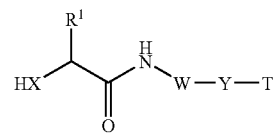

II in which $R^1$, W, Y and T are as defined in claim 1, is reacted with a compound of the formula III

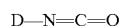

III in which

D is as defined in claim 1, or b) a compound of the formula IV

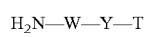

IV in which W, Y and T are as defined in claim 1, is reacted with a compound of the formula V

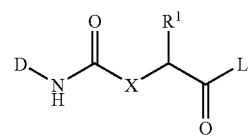

V in which

L is Cl, Br, I or a free or reactively functionally modified OH group, and $R^1$, X and D are as defined in claim 1, and/or c) in that a radical T in a compound of the formula I is converted into another radical T by, for example, i) converting a sulfanyl compound into an imino compound, and/or a base or acid of the formula I is converted into one of its salts.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alcoholates.

The term pharmaceutically usable derivatives is taken to mean, for example, the salts of the compounds according to the invention and also so-called prodrug compounds.

The term prodrug derivatives is taken to mean, for example, compounds of the formula I which have been modified with, for example, alkyl or acyl groups, sugars or oligopeptides and which are rapidly cleaved in the organism to give the effective compounds according to the invention.

These also include biodegradable polymer derivatives of the compounds according to the invention, as described, for example, in Int. J. Pharm. 115, 61–67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

For all radicals which occur more than once, for example A, their meanings are independent of one another.

Above and below, the radicals or parameters D, W, X, Y, T and $R^1$ are as defined under the formula I, unless expressly stated otherwise.

A is alkyl, is unbranched (linear) or branched, and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cycloalkyl is preferably cyclopropyl, cyclobutyl, cyclopentyl, cyclohexyl or cycloheptyl.

Alkylene is preferably methylene, ethylene, propylene, butylene, pentylene or hexylene, furthermore branched alkylene.

$COR^2$ is for example, CHO or —COA.

—COA (acyl) is preferably acetyl, propionyl, furthermore also butyryl, pentanoyl, hexanoyl or, for example, benzoyl.

Hal is preferably F, Cl or Br, but alternatively I.

Ar is, for example, phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)-phenyl, o-, m- or p-acetamidophenyl, o-, m- or p-methoxyphenyl, o-, m- or p-ethoxyphenyl, o-, m- or p-ethoxycarbonylphenyl, o-, m- or p-(N,N-dimethylamino)-phenyl, o-, m- or p-(N,N-dimethylaminocarbonyl)phenyl, o-,m- or p-(N-ethylamino)-phenyl, o-, m- or p-(N,N-diethylamino)-phenyl, o-, m- or p-fluorophenyl, o-, m- or p-bromophenyl, o-, m- or p- chlorophenyl, o-, m- or p-(methylsulfonamido)phenyl, o-, m- or p-(methylsulfonyl)-phenyl, further preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichloroophenyl, 2,4,6-trimethoxyphenyl, 2-hydroxy-3,5-dichlorophenyl, p-iodophenyl, 3,6-dichloro-4-amino-phenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methyl-phenyl, 3-chloro-4-acetamidophenyl or 2,5-dimethyl-4-chlorophenyl.

Ar is preferably, for example, phenyl which is unsubstituted or monosubstituted, disubstituted or trisubstituted by Hal, A, $OR^2$, $SO_2A$, $COOR^2$ or CN phenyl.

Ar is particularly preferably, for example, phenyl which is unsubstituted or monosubstituted or disubstituted by Hal, A, OA, $SO_2A$, $SO_2NH_2$, $COOR^2$ or CN, such as, for example, phenyl, 2-methylsulfonylphenyl, 2-aminosulfonylphenyl, 2-, 3- or 4-chlorophenyl, 4-methylphenyl, 4-bromophenyl, 3-fluoro-4-methoxyphenyl, 4-trifluoromethoxyphenyl, 4-ethoxyphenyl, 2-methoxyphenyl, 3-cyanophenyl or 4-ethoxycarbonylphenyl.

Ar is very particularly preferably unsubstituted phenyl, 4-chlorophenyl or 2-methylsulfonylphenyl.

Y is preferably Het-diyl or Ar-diyl, particularly preferably 1,4-phenylene which is unsubstituted or monosubstituted by A, Cl or F, furthermore also pyridinediyl, preferably pyridine-2,5-diyl or piperidinediyl.

Y is in particular 1,3- or 1,4-phenylene which is unsubstituted or monosubstituted by methyl, ethyl, propyl, Cl or F.

Het is, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5- isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or 5-yl, 1- or 5-tetrazolyl, 1,2,3-oxadiazol4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-quinolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The heterocyclic radicals may also be partially or fully hydrogenated. Het can thus, for example, also be 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-2-, -3- or -4-pyridyl, 1,2,3,4-tetrahydro-1-, -2-, -3-, -4-, -5- or -6-pyridyl, 1-, 2-, 3- or 4-piperidinyl, 2-, 3morpholinyl, tetrahydro-2-, -3- or -4-pyranyl, 1,4-dioxanyl, 1,3-dioxan-2-, 4- or -5-yl, hexahydro-1-, -3- or 4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-,-6-, -7- or -8-quinolyl, 1,2,3,4-tetrahydro-1-,-2-,-3-, -4-, -5-, -6-, -7- or quinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoro-methylenedioxy)phenyl, 2,3-dihydrobenzofuran-5- or 6-yl, 2,3-(2-oxo-methylenedioxy)phenyl or alternatively 3,4-dihydro-2H-1,5-benzodioxepin-6- or -7-yl, furthermore preferably 2,3-dihydrobenzofuranyl or 2,3-dihydro-2-oxofuranyl.

T is preferably a monocyclic or bicyclic saturated, unsaturated or aromatic carbocyclic or heterocyclic ring having from 1 to 3 N, O and/or S atoms which is monosubstituted or disubstituted by =S, =NR$^1$, =NOR$^2$, =NCOR$^2$, =NCOOR$^2$, =NOCOR$^2$, =N—CN or =N—NO$_2$ and may furthermore be monosubstituted or disubstituted by Hal, A, CONH$_2$ or COOA.

T is, in particular, piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-methylimidazolidin-1-yl, each of which is monosubstituted or disubstituted by =NR$^2$, =S, =NOR$^2$ or =N—CN.

T is furthermore particularly preferably, for example, piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted or disubstituted by =NR$^2$, =S, =NOR$^2$ or =N—CN, where the thiadiazole ring may additionally be substituted by A, CONH$_2$ or COOA, very particularly preferably 2-iminopiperidin-1-yl and the corresponding hydroxylamino, thioxo and =N—(CH$_2$)$_{1-3}$NA'$_2$ derivatives, where A' is alkyl having 1, 2, 3, 4, 5 or 6 carbon atoms.

In a further embodiment, T is 2-iminopiperidin-1-yl, 2-iminopyrrolidin-1-yl, 2-hydroxyiminopiperidin-1-yl, 2-hydroxyiminopyrrolidin-1-yl, 2-methoxy-iminopiperidin-1-yl, 2-methoxyiminopyrrolidin-1-yl, 2-cyaniminoimidazolidin-1-yl or 2-cyanimino-3-methylimidazolidin-1-yl.

D is in particular, for example, phenyl which is unsubstituted or monosubstituted or disubstituted by Hal, A, hydroxyl, methoxy, ethoxy, hydroxycarbonyl, methoxycarbonyl or ethoxycarbonyl, oris pyridyl or thienyl, each of which is unsubstituted or monosubstituted by Hal.

D is very particularly preferably 4-chlorophenyl or 3-chloro-2-pyridyl.

R$^1$ is preferably, for example, H, phenyl or thienyl, each of which is unsubstituted or monosubstituted or disubstituted by Hal and/or A,
or alkyl having 1–6 carbon atoms, which may be substituted by thiophene, imidazole, indole, S(O)$_m$R$^2$, OR$^2$, cycloalkyl or phenyl, where the imidazole ring can have a substituent A, R$^1$ in a further preferred embodiment is alternatively Het', where Het' is preferably a 5- or 6-membered heterocyclic ring having one or two N, O or S atoms, for example 2-thienyl or 2-furyl.

Specifically, R$^1$ is preferably H, phenyl, 2-fluorophenyl, 2-chlorophenyl, alkyl having 1, 2, 3, 4, 5 or 6 carbon atoms, thienyl, methoxymethyl, (1-methyl-1H-imidazolyl-4-yl)methyl or methylsulfonylethyl.

R$^2$ is preferably, for example, H or alkyl having 1, 2, 3, 4, 5 or 6 carbon atoms.

n is preferably 0 or 1.

m is preferably 2.

Y is preferably, for example, 1,4-phenylene which is unsubstituted or monosubstituted by alkyl.

W is preferably absent.

The compounds of the formula I can have one or more centres of chirality and can therefore occur in various stereoisomeric forms. The formula I covers all these forms.

Accordingly, the invention relates, in particular, to compounds of the formula I in which at least one of the said radicals has one of the preferred meanings indicated above. Some preferred groups of compounds can be expressed by the following sub-formulae Ia to Iq, which conform to the formula I and in which the radicals not designated in greater detail are as defined for the formula I, but in which in Ia D is phenyl which is unsubstituted or monosubstituted or disubstituted by Hal, A, OR$^2$ or COOR$^2$ or is pyridyl or thienyl, each of which is unsubstituted or monosubstituted by Hal;

in Ib R$^2$ is H or alkyl having 1, 2, 3, 4, 5 or 6 carbon atoms;

in Ic R$^1$ is H, phenyl or thienyl, each of which is unsubstituted or monosubstituted or disubstituted by Hal and/or A, or is alkyl having 1-6 carbon atoms, which may be substituted by thiophene, imidazole, indole, S(O)$_m$R$^2$, OR$^2$, cycloalkyl or phenyl, where the imidazole ring may have a substituent A;

in Id X is NH or O;

in Ie W is (CH$_2$)$_n$;

in If Y is Ar-diyl or Het-diyl;

in Ig T is a monocyclic or bicyclic saturated, unsaturated or aromatic carbocyclic or heterocyclic ring having from 1 to 3 N, O and/or S atoms which is monosubstituted or disubstituted by =S, =NR$^2$, =NOR$^2$, =NCOR$^2$, =NCOOR$^2$, =NOCOR$^2$, =N—CN or =N—NO$_2$ and may furthermore be monosubstituted or disubstituted by Hal, A, CONH$_2$ or COOA;

in Ih T is a monocyclic or bicyclic saturated or unsaturated heterocyclic ring having 1 or 2 N and/or O atoms which is monosubstituted or disubstituted by =NR$^2$, =S, =NOR$^2$, =N—CN or =N—NO$_2$;

in Ii T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted or disubstituted by =NR$^2$, =S, =NOR$^2$ or =N—CN, where the thiadiazole ring may additionally be substituted by A, CONH$_2$ or COOA, A' is alkyl having 1, 2, 3, 4, 5 or 6 carbon atoms, in which 1–7 H atoms may be replaced by F;

in Ij T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted or disubstituted by =NR$^{2b}$, =S, =NOR$^{2b}$ or =N—CN, where the thiadiazole ring may additionally be substituted by A, CONH$_2$ or COOA, R$^{2b}$ is H, OH or OA', A' is alkyl having 1, 2, 3, 4, 5 or 6 carbon atoms, in which 1–7 H atoms may be replaced by F;

in Ik T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted or disubstituted by $=NR^{2b}$, $=S$, $=NOR^{2b}$ or $=N-CN$, $R^{2b}$ is H, OH or OA", A" is methyl, ethyl, propyl, isopropyl or butyl;

in Il Ar is phenyl which is unsubstituted or monosubstituted or disubstituted by Hal, A, OA, $SO_2A$, $COOR^2$, $SO_2NH_2$ or CN;

in Im D is phenyl which is unsubstituted or monosubstituted by Hal or is pyridyl or thienyl, each of which is unsubstituted or monosubstituted by Hal, $R^1$ is H, phenyl or thienyl, each of which is unsubstituted or monosubstituted or disubstituted by Hal and/or A, or is alkyl having 1–6 carbon atoms, which may be substituted by thiophene, imidazole, indole, $S(O)_mR^2$, $OR^2$, cycloalkyl or phenyl, where the imidazole ring may have a substituent A, X is NH or O, W is absent, Y is Ar-diyl, pyridinediyl or piperidinediyl, Ar is phenyl which is unsubstituted or monosubstituted or disubstituted by Hal, A, OA, $SO_2A$, $COOR^2$, $SO_2NH_2$ or CN, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by $=NR^{2b}$, $=S$, $=NOR^{2b}$ or $=N-CN$, where the thiadiazole ring may additionally be substituted by A, $CONH_2$ or COOA, $R^{2b}$ is H, OH or OA", A" is methyl, ethyl, propyl, isopropyl or butyl;

in In D is phenyl which is unsubstituted or monosubstituted by Hal or is pyridyl or thienyl, each of which is unsubstituted or monosubstituted by Hal, $R^1$ is H, phenyl or thienyl, each of which is unsubstituted or monosubstituted or disubstituted by Hal and/or A, or is alkyl having 1–6 carbon atoms, which may be substituted by thiophene, imidazole, indole, $S(O)_mR^2$, $OR^2$, cycloalkyl or phenyl, where the imidazole ring may have a substituent A, X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by $=NR^{2b}$, $=S$, $=NOR^{2b}$ or $=N-CN$, where the thiadiazole ring may additionally be substituted by A, $CONH_2$ or COOA, $R^{2b}$ is H, OH or OA", A" is methyl, ethyl, propyl, isopropyl or butyl;

in Io D is phenyl or thienyl, each of which is unsubstituted or monosubstituted by Hal, $R^1$ is H, phenyl which is unsubstituted or monosubstituted by Hal, or alkyl having 1–6 carbon atoms, X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted by $=NR^{2b}$, $=S$, $=NOR^{2b}$ or $=N-CN$, $R^{2b}$ is H, OH or OA", A" is methyl, ethyl, propyl, isopropyl or butyl;

in Ip D is phenyl or thienyl, each of which is unsubstituted or monosubstituted by Hal, $R^1$ is H, phenyl which is unsubstituted or monosubstituted by Hal, alkyl having 1-6 carbon atoms or $Het^1$, X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted by $=NR^{2b}$, $=S$, $=NOR^{2b}$ or $=N-CN$, $R^{2b}$ is H, OH or OA", A" is methyl, ethyl, propyl, isopropyl or butyl, Het' is 2-thienyl or 2-furyl;

in Iq D is phenyl or thienyl, each of which is unsubstituted or monosubstituted by Hal, $R^1$ is H, phenyl which is unsubstituted or monosubstituted or disubstituted by Hal and/or A, alkyl having 1-6 carbon atoms or Het', or alkyl having 1-6 carbon atoms which may be substituted by thiophene, imidazole, indole, $S(O)_mA"$, OA", cycloalkyl or phenyl, where the imidazole ring may have a substituent A", X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by $=NR^{2b}$, $=S$, $=NOR^{2b}$ or $=N-CN$, where the thiadiazole ring may additionally be substituted by A", $CONH_2$ or COOA", $R^{2b}$ is H, OH or OA", A" is methyl, ethyl, propyl, isopropyl or butyl, Het' is 2-thienyl or 2-furyl, and pharmaceutically usable derivatives, solvates and stereoisomers thereof, including mixtures thereof in all ratios.

The compounds of the formula I and also the starting materials for the preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds of the formulae II, III, IV and V are generally known. If they are novel, they can, however, be prepared by methods known per se.

All compounds of the following formula VI (where R=H or methyl; n=3, 4 or 5) can be synthesised in accordance with the following scheme:

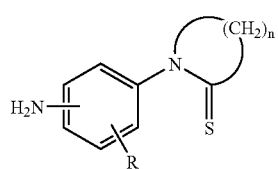

For example, synthesis of 1-(4-amino-2-methylphenyl)piperidine-2-thione:

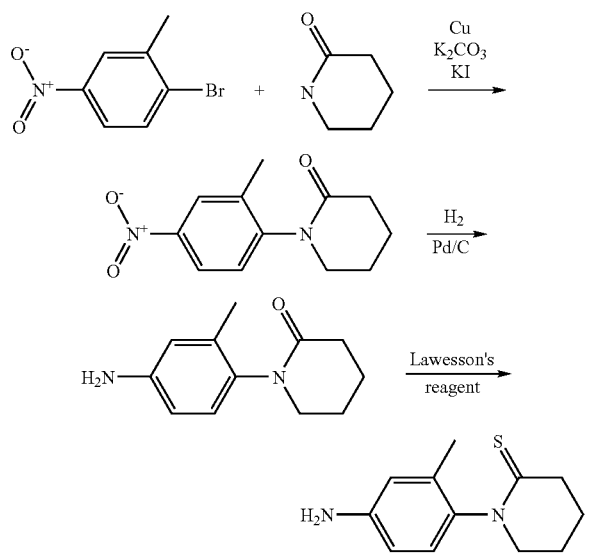

Alternative synthesis:

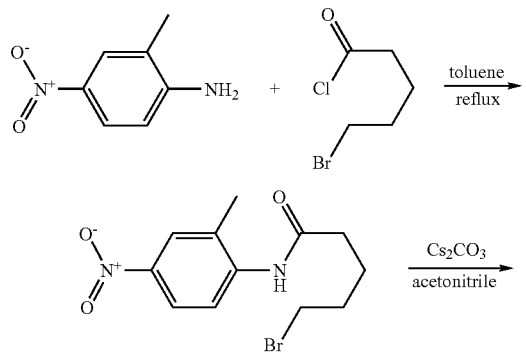

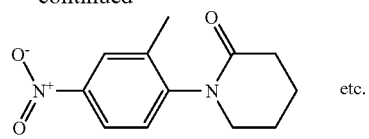

Synthesis of the phenylpiperidinethione unit without a methyl group:

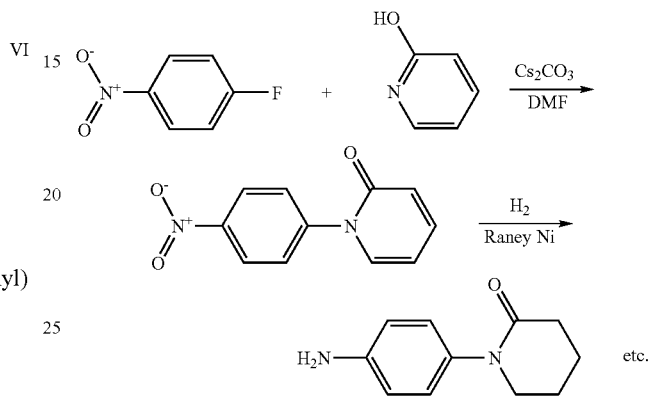

Compounds of the formula I can preferably be obtained by reacting compounds of the formula II with compounds of the formula III.

The reaction is generally carried out in an inert solvent, in the presence of an acid-binding agent, preferably an alkali or alkaline earth metal hydroxide, carbonate or bicarbonate or another salt of a weak acid of the alkali or alkaline earth metals, preferably of potassium, sodium, calcium or caesium. The addition of an organic base, such as triethylamine, dimethylaniline, pyridine or quinoline, or of an excess of the phenol component of the formula II or of the alkylation derivative of the formula III, may also be favourable. Depending on the conditions used, the reaction time is between a few minutes and 14 days, and the reaction temperature is between about 0° and 150°0, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitrites, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Compounds of the formula I can furthermore be obtained by reacting compounds of the formula IV with compounds of the formula V.

The reaction is generally carried out in an inert solvent and under conditions as indicated above.

In the compounds of the formula V, L is preferably Cl, Br, I or a free or reactively modified OH group, such as, for example, an activated ester, an imidazolide or alkylsulfonyloxy having 1-6 carbon atoms (preferably methylsulfonyloxy or trifluoromethylsulfonyloxy) or arylsulfonyloxy having 6–10 carbon atoms (preferably phenyl- or p-tolylsulfonyloxy).

Radicals of this type for activation of the carboxyl group in typical acylation reactions are described inn the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

The reaction is generally carried out in an inert solvent, in the presence of an acid-binding agent, preferably an organic base, such as DIPEA, triethylamine, dimethylaniline, pyridine or quinoline, or an excess of the carboxyl component of the formula V.

It may also be favourable to add an alkali or alkaline earth metal hydroxide, carbonate or bicarbonate or another salt of a weak acid of the alkali or alkaline earth metals, preferably of potassium, sodium, calcium or caesium.

Depending on the conditions used, the reaction time is between a few minutes and 14 days, and the reaction temperature is between about −30° and 140°, normally between −10° and 90°, in particular between about 0° and about 70°.

Suitable inert solvents are those mentioned above.

Compounds of the formula I can furthermore be obtained by liberating compounds of the formula I from one of their functional derivatives by treatment with a solvolysing or hydrogenolysing agent.

Preferred starting materials for the solvolysis or hydrogenolysis are those which conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'—N group, in which R' is an amino-protecting group, instead of an HN group, and/or those which carry an hydroxyl-protecting group instead of the H atom of an hydroxyl group, for example those which conform to the formula I, but carry a —COOR" group, in which R" is an hydroxyl-protecting group, instead of a —COOH group.

Preferred starting materials are also the oxadiazole derivatives, which can be converted into the amidino compounds.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1–20, in particular 1–8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easily removable after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1–20, in particular 1–10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5N HCl in dioxane at 15–30°, and the FMOC group can be cleaved off using an approximately 5 to 50% solution of dimethylamine, diethylamine or piperidine in DMF at 15–30°.

Protecting groups which can be removed hydrogenolytically (for example CBZ, benzyl or the liberation of the amidino group from its oxadiazole derivative) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20–30° and 1–10 bar. Hydrogenolysis of the CBZ group succeeds well, for example, on 5 to 10% Pd/C in methanol or using ammonium formate (instead of hydrogen) on Pd/C in methanol/DMF at 20–30°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether(diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline) or N-benzenesulfonylproline), or the various optically active camphorsulfonic acids. Also advantage is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Examples of suitable eluents for this purpose are aqueous or alcoholic solvent mixtures, such as, for example, hexane/isopropanol/acetonitrile, for example in the ratio 82:15:3.

The invention furthermore relates to the use of compounds of the formula I and/or their physiologically acceptable salts for the preparation of a medicament (pharmaceutical preparation), in particular by non-chemical methods. They can be converted here into a suitable dosage form together with at least one solid, liquid and/or semiliquid excipient or assistant and, if desired, in combination with one or more further active ingredients.

The invention furthermore relates to medicaments comprising at least one compound of the formula I and/or its pharmaceutically usable derivatives, solvates and stereoisomers, including mixtures thereof in all ratios, and optionally excipients and/or assistants.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatin, carbohydrates, such as lactose or starch, magnesium stearate, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise assistants, such as lubricants, preservatives, stabilisers and/or wetting agents, emulsifying agents, salts for modifying the osmotic pressure, buffer substances, colorants and flavours and/or a plurality of further active ingredients, for example one or more vitamins.

The compounds of the formula I and their physiologically acceptable salts can be used for combating thromboembolic diseases, such as thrombosis, myocardial infarction, arteriosclerosis, inflammation, apoplexia, angina pectoris, restenosis after angioplasty, claudicatio intermittens, migraine, tumours, tumour diseases and/or tumour metastases.

In general, the substances according to the invention are preferably administered in doses between about 1 and 500 mg, in particular between 5 and 100 mg, per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular disease to which the therapy applies. Oral administration is preferred.

The invention furthermore relates to medicaments comprising at least one compound of the formula I and/or its pharmaceutically usable derivatives, solvates and stereoisomers, including mixtures thereof in all ratios, and at least one further medicament active ingredient.

The invention also relates to a set (kit) consisting of separate packs of
  (a) an effective amount of a compound of the formula I and/or its pharmaceutically usable derivatives, solvates and stereoisomers, including mixtures thereof in all ratios, and
  (b) an effective amount of a further medicament active ingredient.

The set comprises suitable containers, such as boxes, individual bottles, bags or ampoules. The set may, for example, comprise separate ampoules each containing an effective amount of a compound of the formula I and/or its pharmaceutically usable derivatives, solvates and stereoisomers, including mixtures thereof in all ratios, and an effective amount of a further medicament active ingredient in dissolved or lyophilised form.

The invention furthermore relates to the use of compounds of the formula I and/or their pharmaceutically usable derivatives, solvates and stereoisomers, including mixtures thereof in all ratios, for the preparation of a medicament for the treatment of thromboses, myocardial infarction, arteriosclerosis, inflammation, apoplexia, angina pectoris, restenosis after angioplasty, claudicatio intermittens, migraine, tumours, tumour diseases and/or tumour metastases, in combination with at least one further medicament active ingredient.

Above and below, all temperatures are given in ° C. In the following examples, 'conventional work-up' means that water is added if necessary, the pH is adjusted, if necessary, to between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M⁺
  FAB (fast atom bombardment) (M+H)⁺
  ESI (electrospray ionisation) (M+H)⁺ (unless stated otherwise)

EXAMPLE 1

Preparation of Amine Units a)
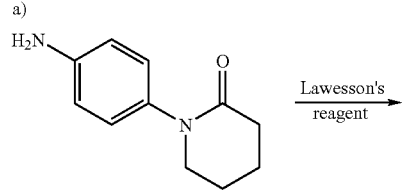

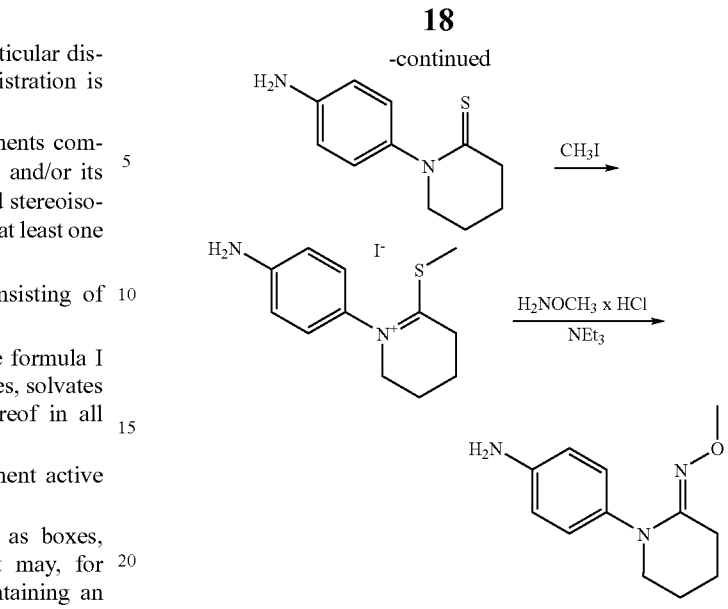

15 g (78.8 mmol) of 1-(4-aminophenyl)piperidin-2-one are heated to the boil together with 16.0 g (39.5 mmol) of 2,4-bis(4-methoxyphenyl)-1,3,2,4-dithiadiphosphetane 2,4-disulfide (Lawesson's reagent) in 100 ml of anhydrous toluene. After 45 minutes, the solvent is evaporated, and the residue is taken up in dichloromethane and 2 N HCl. The aqueous phase is extracted three times with dichloromethane and adjusted to a pH of 12 using conc. NaOH. Extraction with dichloromethane, drying over sodium sulfate and evaporation of the solvent give 1-(4-aminophenyl)piperidine-2-thione as a colourless solid, ESI 207.

1.25 ml (20.0 mmol) of iodomethane are added to a solution of 3.74 g (18.1 mmol) of 1-(4-aminophenyl)piperidine-2-thione in 30 ml of acetone, and the mixture is stirred at room temperature for 48 hours. The reaction mixture is evaporated, giving 1-(4-aminophenyl)-6-methylsulfanyl-2,3,4,5-tetrahydropyridinium iodide as a brownish solid; ESI 221.

3.5 ml (25 mmol) of triethylamine are added to a solution of 2.68 g (12.1 mmol) of 1-(4-aminophenyl)-6-methylsulfanyl-2,3,4,5-tetrahydro-pyridinium iodide and 1.01 g (12.1 mmol) of O-methylhydroxylammonium chloride in 30 ml of ethanol, and the mixture is stirred at room temperature for 20 hours. The reaction mixture is evaporated and taken up in water, and the resultant precipitate is filtered off, giving 1-(4-aminophenyl)-piperidin-2-one O-methyl oxime as a colourless solid; ESI 220.

b)

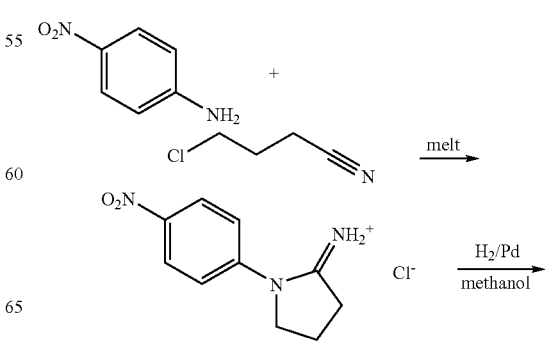

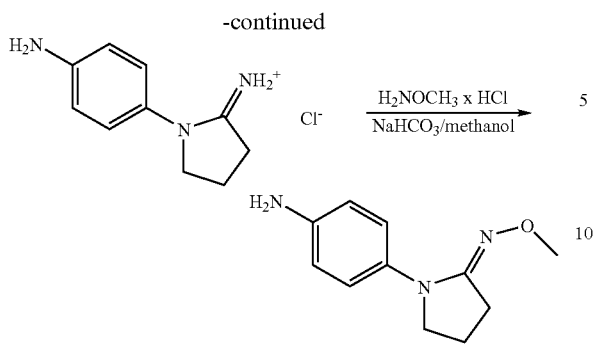

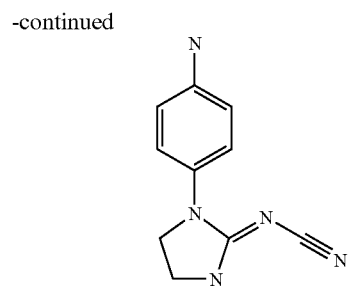

A mixture of 40.0 g (290 mmol) of 4-nitroaniline and 40.0 ml (421 mmol) of 4-chlorobutyronitrile is heated at the boil (about 190° C.) for 30 minutes using a hot-air fan. The mixture is allowed to cool and is digested with ethyl acetate, giving 1-(4-nitrophenyl)pyrrolidin-2-ylideneamine, hydrochloride, as a brown solid, ESI 206.

2.5 g of water-moist palladium on activated carbon (5% of Pd) are added to a solution of 25.0 g (103 mmol) of 1-(4-nitrophenyl)pyrrolidin-2-ylideneamine, hydrochloride, in 500 ml of methanol, and the mixture is hydrogenated at room temperature for 17 hours. The catalyst is filtered off, and the filtrate is evaporated, giving 1-(4-aminophenyl)pyrrolidin-2-ylideneamine, hydrochloride, as a brownish solid; ESI 176.

2.68 g (12.7 mmol) of 1-(4-aminophenyl)pyrrolidin-2-ylideneamine, hydrochloride, are dissolved in 70 ml of methanol, 9.49 g (113 mmol) of sodium hydrogencarbonate and 4.06 g (48.6 mmol) of methoxylamine, hydrochloride, are added, and the mixture is heated at 70° C. for 48 hours. The reaction mixture is evaporated, and the residue is taken up in acetone. The insoluble components are filtered off, and the filtrate is evaporated. The residue is chromatographed on a silica-gel column with ethyl acetate as eluent, giving 1-(4-aminophenyl)pyrrolidin-2-one O-methyl oxime as a brownish solid; ESI 206.

23.63 g (150 mmol) of 4-chloronitrobenzene are dissolved in 92.1 ml (1.38 mol) of ethylenediamine and heated to the boil under a nitrogen atmosphere. After 24 hours, the mixture is evaporated to dryness, and the crude product is suspended in 100 ml of 1 N sodium hydroxide solution and filtered off. Washing with water and drying under reduced pressure gives 25.9 g of $N^1$-(4-nitrophenyl)ethane-1,2-diamine in the form of yellow crystals (ESI 182).

5.9 g (32.56 mmol) of $N^1$-(4-nitrophenyl)ethane-1,2-diamine are suspended in 200 ml of acetonitrile, and 3.72 g of dimethyl N-cyanimidocarbonate and 6.75 g of $K_2CO_3$ are added. After the mixture has been stirred at room temperature for 2 hours, conventional work-up gives 5.16 g of 1-(4-nitrophenyl)imidazolidin-2-ylidene cyanamide (ESI: 232).

3.47 g (15 mmol) of 1-(4-nitrophenyl)imidazolidin-2-ylidene cyanamide are hydrogenated in 35 ml of methanol using hydrogen on 5% palladium on carbon. Conventional work-up gives 2.88 g of 1-(4-aminophenyl)imidazolidin-2-ylidene cyanamide in the form of a pale-brown solid (ESI: 202).

Preparation of 2-[N-(4-chlorophenyl)carbamoyloxy]-N-[4-(2-iminopiperidin-1-yl)phenyl]-2-phenylacetamide c)

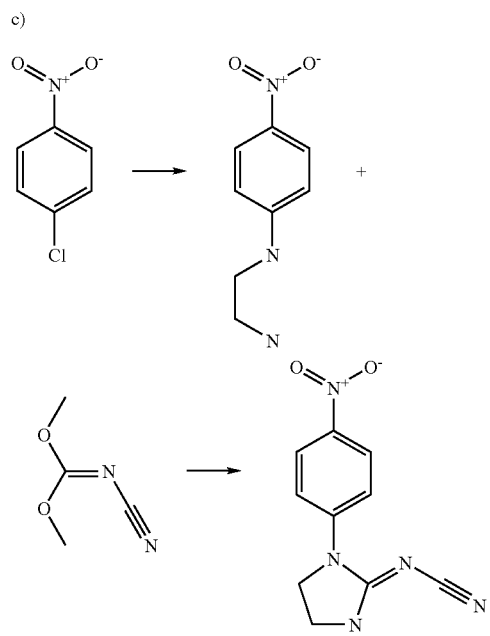

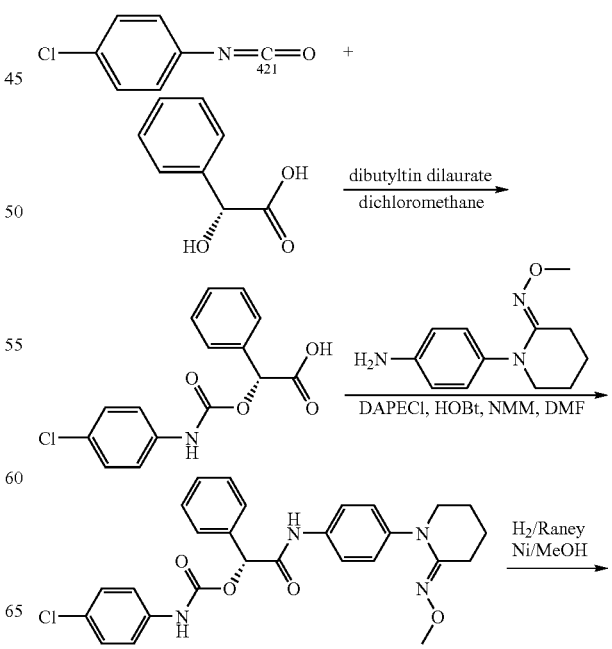

-continued

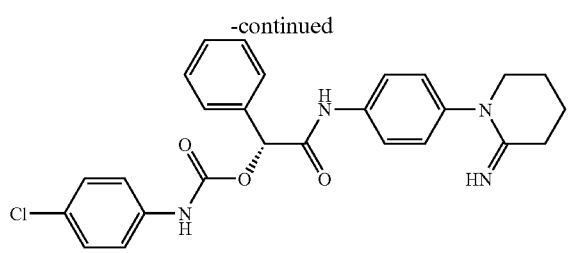

1.1 400 mg (0.63 mmol) of dibutyltin dilaurate are added to a solution of 10.0 g (65.7 mmol) of (R)-mandelic acid and 10.0 g (65.1 mmol) of 4-chlorophenyl isocyanate in 100 ml of dichloromethane, and the mixture is stirred at room temperature for 24 hours. The reaction mixture is introduced into water and extracted with ethyl acetate. The organic phase is evaporated, giving (R)-(4-chlorophenylcarbamoyloxy)phenylacetic acid as a colourless solid; ESI 306.

1.2 101 mg (1.00 mmol) of 4-methylmorpholine are added to a solution of 183 mg (0.600 mmol) of (R)-(4-chlorophenylcarbamoyloxy)phenylacetic acid, 129 mg (0.588 mmol) of 1-(4-aminophenyl)piperidin-2-one O-methyl oxime, 192 mg (1.00 mmol) of N-(3-dimethylaminopropyl)-N'-ethylcarbodiimide hydrochloride (DAPECI) and 91.9 mg (0.600 mmol) of hydroxybenzotriazole hydrate (HOBt) in 1 ml of DMF, and the mixture is stirred at room temperature for 24 hours. The reaction mixture is introduced into saturated sodium hydrogencarbonate solution, and the resultant precipitate is filtered off. The precipitate is chromatographed on a silica-gel column with petroleum ether/ethyl acetate as eluent, giving (R)-2-[N-(4-chlorophenyl)carbamoyloxy]-N-[4-(2-methoxyiminopiperidin-1-yl)phenyl]-2-phenylacetamide ("AA") as a colourless solid; ESI 507.

1.3 0.3 g of water-moist Raney nickel is added to a solution of 50 mg (0.099 mmol) of [4-(2-methoxyiminopiperidin-1-yl)phenylcarbamoyl]phenylmethyl (R)-(4-chlorophenyl)carbamate in 10 ml of methanol, and the mixture is hydrogenated. The reaction mixture is filtered, and the filtrate is evaporated. The residue is chromatographed on a silica-gel column with dichloromethane/methanol as eluent, giving (R)-2-[N-(4-chlorophenyl)carbamoyloxy]-N-[4-(2-iminopiperidin-1-yl)phenyl]-2-phenylacetamide as a colourless solid; ESI 477.

1.4 30 mg (0.063 mmol) of [4-(2-iminopiperidin-1-yl)phenylcarbamoyl]-phenylmethyl (R)-(4-chlorophenyl)carbamate are dissolved in 0.063 ml of 1 N HCl and lyophilised, giving (R)-2-[N-(4-chlorophenyl)carbamoyloxy]-N-[4-(2-iminopiperidin-1-yl)phenyl]-2-phenylacetamid, hydrochloride ("AB") as a colourless solid; ESI 477.

The following compounds are obtained analogously:
(R)-2-[N-(4-chlorophenyl)carbamoyloxy]-N-[4-(2-iminopiperidin-1-yl)-3-methylphenyl]-2-phenylacetamide, hydrochloride, ESI 491;
(R)-2-[N-(4-chlorophenyl)carbamoyloxy]-N-[4-(2-iminopyrrolidin-1-yl)-3-methylphenyl]-2-phenylacetamide, hydrochloride, ESI 477;
(R)-2-[N-(4-chlorophenyl)carbamoyloxy]-N-[4-(2-iminopiperidin-1-yl)-phenyl]-2-(2-fluorophenyl)acetamide,
2-[N-(4-chlorophenyl)carbamoyloxy]-N-[4-(2-iminopiperidin-1-yl)-phenyl]-2-(2-chlorophenyl)acetamide,
(S)-2-[N-(4-chlorophenyl)carbamoyloxy]-N-[4-(2-iminopiperidin-1-yl)-phenyl]-2-phenylacetamide,
2-[N-(4-chlorophenyl)carbamoyloxy]-N-[4-(2-iminopiperidin-1-yl)-phenyl]propionamide,
(R)-2-[N-(5-chloropyridin-2-yl)carbamoyloxy]-N-[4-(2-iminopiperidin-1-yl)phenyl]-2-phenylacetamide,
(R)-2-[N-(4-chlorophenyl)carbamoyloxy]-N-[4-(2-iminopyrrolidin-1-yl)-phenyl]-2-phenylacetamide,
(R)-2-[N-(4-chlorophenyl)carbamoyloxy]-N-[4-(2-iminopyrrolidin-1-yl)-phenyl]-2-(2-fluorophenyl)acetamide,
(R)-2-[N-(4-chlorophenyl)carbamoyloxy]-N-[4-(2-imino-2H-pyridin-1-yl)phenyl]-2-phenylacetamide,
(R)-2-[N-(5-chlorothiophen-2-yl)carbamoyloxy]-N-[4-(2-iminopiperidin-1-yl)phenyl]-2-phenylacetamide,
(R)-2-[N-(4-chlorophenyl)carbamoyloxy]-N-[4-(3-iminomorpholin-4-yl)-phenyl]-2-phenylacetamide,
2-[N-(4-chlorophenyl)carbamoyloxy]-N-[4-(2-methoxyiminopiperidin-1-yl)-3-methylphenyl]-2-(2-chlorophenyl)acetamide, ESI 555;
(R)-2-[N-(4-chlorophenyl)carbamoyloxy]-N-[4-(2-methoxyiminopiperidin-1-yl)-3-methylphenyl]-2-phenylacetamide, ESI 521;
(S)-2-[N-(4-chlorophenyl)carbamoyloxy]-N-[4-(2-methoxyiminopiperidin-1-yl)-3-methylphenyl]-2-phenylacetamide, ESI 521;
(R)-2-[N-(4-chlorophenyl)carbamoyloxy]-N-[4-(2-methoxyiminopyrrolidin-1-yl)phenyl]-2-phenylacetamide, ESI 493;
(R)-2-[N-(4-chlorophenyl)carbamoyloxy]-N-[4-(2-methoxyiminopiperidin-1-yl)-3-methylphenyl]-2-(2-chlorophenyl)acetamide, ESI 555;
(R)-2-[N-(4-chlorophenyl)carbamoyloxy]-N-[4-(2-azabicyclo[2.2.2]-octan-3-imino-2-yl)phenyl]-2-phenylacetamide.

EXAMPLE 2

Preparation of (R)-2-[3-(4-chlorophenyl)ureido]-N-[4-(2-iminopiperidin-1-yl)-3-methylphenyl]-2-phenylacetamide

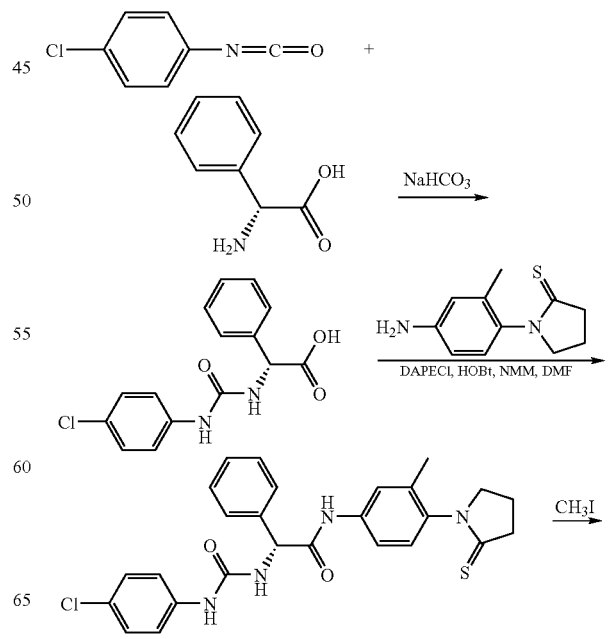

-continued

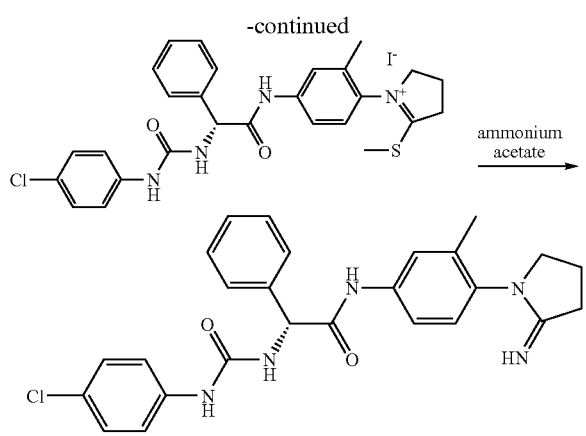

2.1 A solution of 10.0 g (66.2 mmol) of (R)-alpha-aminophenylacetic acid in 600 ml of 0.25 M aqueous sodium hydrogencarbonate solution is heated to 80° C., and 20.2 g (132 mmol) of 4-chlorophenyl isocyanate are added. The reaction mixture is stirred at this temperature for 1 hour and cooled in an ice bath, and the resultant precipitate is filtered off. The filtrate is acidified using 2 N HCl, and the resultant precipitate is filtered off, giving (R)-[3-(4-chlorophenyl)ureido]phenylacetic acid as a colourless solid; ESI 305.

2.2 152 mg (1.50 mmol) of 4-methylmorpholine are added to a solution of 366 mg (1.20 mmol) of (R)-[3-(4-chlorophenyl)ureido]phenylacetic acid, 248 mg (1.20 mmol) of 1-(4-amino-2-methylphenyl)pyrrolidine-2-thione, 249 mg (1.30 mmol) of N-(3-dimethylaminopropyl)-N'-ethylcarbodiimide hydrochloride (DAPECI) and 184 mg (1.20 mmol) of hydroxybenzotriazole hydrate (HOBt) in 1 ml of DMF, and the mixture is stirred at room temperature for 24 hours. The reaction mixture is introduced into saturated sodium hydrogencarbonate solution, and the resultant precipitate is filtered off, giving (R)-2-[3-(4-chlorophenyl)ureido]-N-[3-methyl-4-(2-thioxopyrrolidin-1-yl)phenyl]-2-phenylacetamide as a colourless solid; ESI 493.

2.3 78.1 μl (1.25 mmol) of iodomethane are added to a solution of 380 mg (0.771 mmol) of (R)-2-[3-(4-chlorophenyl)ureido]-N-[3-methyl-4-(2-thioxopyrrolidin-1-yl)phenyl]-2-phenylacetamide in 10 ml of acetone, and the mixture is stirred at room temperature for 24 hours. The reaction mixture is evaporated, and the residue is taken up in tert-butyl methyl ether. The resultant precipitate is filtered off, giving (R)-1-(4-{2-[3-(4-chlorophenyl)ureido]-2-phenylacetylamino}-2-methylphenyl)-5-methylsulfanyl-3,4-dihydro-2H-pyrrolium iodide as a colourless solid; ESI 507.

2.4 308 mg (4.00 mmol) of ammonium acetate are added to a solution of 469 mg (0.739 mmol) of (R)-1-(4-{2-[3-(4-chlorophenyl)ureido]-2-phenyl-acetylamino}-2-methylphenyl)-5-methylsulfanyl-3,4-dihydro-2H-pyrrolium iodide in 30 ml of ethanol, and the mixture is heated at the boil for 24 hours. The reaction mixture is evaporated, and the residue is taken up in water. The resultant precipitate is filtered off, giving (R)-2-[3-(4-chlorophenyl)ureido]-N-[4-(2-iminopyrrolidin-1-yl)-3-methylphenyl]-2-phenylacetamide as a colourless solid; ESI 476.

2.5 170 mg (0.357 mmol) of (R)-2-[3-(4-chlorophenyl)ureido]-N-[4-(2-iminopyrrolidin-1-yl)-3-methylphenyl]-2-phenylacetamide are dissolved in 2 ml of 0.1 N HCl in 2-propanol, and tert-butyl methyl ether is added. The resultant precipitate is filtered off, giving (R)-2-[3-(4-chlorophenyl)ureido]-N-[4-(2-iminopyrrolidin-1-yl)-3-methylphenyl]-2-phenylacetamide, hydrochloride ("BA") as a colourless solid; ESI 476.

The following compounds are obtained analogously:
(R)-2-[3-(4-chlorophenyl)ureido]-N-[4-(2-iminopiperidin-1-yl)-3-methylphenyl]-2-phenylacetamide, hydrochloride, ESI 490;
(R)-2-[3-(4-chlorophenyl)ureido]-N-[4-(2-iminopiperidin-1-yl)-phenyl]-2-phenylacetamide,
(S)-2-[3-(4-chlorophenyl)ureido]-N-[4-(2-iminopiperidin-1-yl)-phenyl]-2-phenylacetamide,
(R)-2-[3-(4-chlorophenyl)ureido]-N-[4-(2-iminopiperidin-1-yl)-phenyl]propionamide,
(R)-2-[3-(4-chlorophenyl)ureido]-N-[4-(2-iminopiperidin-1-yl)-phenyl]-2-(2-fluorophenyl)acetamide,
(R)-2-[3-(4-chlorophenyl)ureido]-N-[4-(2-iminopiperidin-1-yl)-phenyl]valeramide,
(R)-2-[3-(4-chlorophenyl)ureido]-N-[4-(2-iminopyrrolidin-1-yl)-phenyl]-2-(2-fluorophenyl)acetamide,
(R)-2-[3-(5-chlorothiophen-2-yl)ureido]-N-[4-(2-iminopiperidin-1-yl)-phenyl]-2-phenylacetamide,
(S)-2-[3-(4-chlorophenyl)ureido]-N-[4-(2-methoxyiminopiperidin-1-yl)-3-methylphenyl]-2-phenylacetamide, ESI 520;
(R)-2-[3-(4-chlorophenyl)ureido]-N-[4-(2-methoxyiminopyrrolidin-1-yl)phenyl]-2-phenylacetamide, ESI 492.

EXAMPLE 3

Preparation of (R)-2-[3-(4-chlorophenyl)ureido]-N-[4-(2-iminopyrrolidin-1-yl)phenyl]-2-phenylacetamide

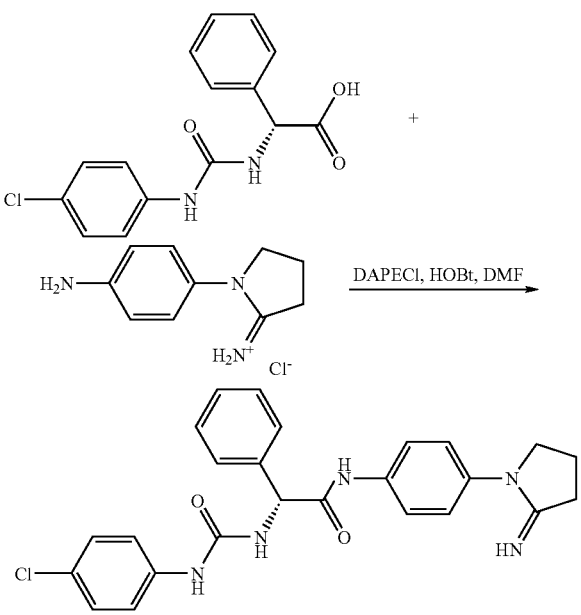

3.1 A solution of 366 mg (1.20 mmol) of (R)-[3-(4-chlorophenyl)-ureido]phenylacetic acid, 254 mg (1.20 mmol) of 1-(4-aminophenyl)pyrrolidin-2-ylideneamine hydrochloride, 230 mg (1.20 mmol) of N-(3-dimethylaminopropyl)-N'-ethylcarbodiimide hydrochloride (DAPECI)

and 184 mg (1.20 mmol) of hydroxybenzotriazole hydrate (HOBt) in 1 ml of DMF is stirred at room temperature for 24 hours. The reaction mixture is introduced into saturated sodium hydrogencarbonate solution, and the resultant precipitate is filtered off, giving (R)-2-[3-(4-chlorophenyl)ureido]-N-[4-(2-iminopyrrolidin-1-yl)phenyl]-2-phenylacetamide as a colourless solid; ESI 462.

3.2 260 mg (0.563 mmol) of (R)-2-[3-(4-chlorophenyl)ureido]-N-[4-(2-iminopyrrolidin-1-yl)phenyl]-2-phenylacetamide are dissolved in 5.6 ml of 0.1 N HCl in 2-propanol, and tert-butyl methyl ether is added. The resultant precipitate is filtered off, giving (R)-2-[3-(4-chlorophenyl)ureido]-N-[4-(2-iminopyrrolidin-1-yl)phenyl]-2-phenylacetamide, hydrochloride, as a colourless solid; ESI 462.

The following compound is obtained analogously:
(R)-2-[3-(4-chlorophenyl)ureido]-N-[4-(2-iminopyrrolidin-1-yl)-phenyl]-2-(thiophen-2-yl)acetamide, hydrochloride, ESI 468.

EXAMPLE 4

Reaction of the corresponding carboxylic acids with the amine described in Example 1 c) analogously to Example 3 gives the following compounds:
(R)-2-[3-(4-chlorophenyl)ureido]-N-[4-(2-cyaniminoimidazolidin-1-yl)phenyl]-2-phenylacetamide, ESI 489;
(R)-2-[3-(4-chlorophenyl)ureido]-N-[4-(2-cyaniminoimidazolidin-1-yl)phenyl]-2-thiophen-2-ylacetamide ("CA"), ESI 495;
(R)-2-[3-(4-chlorophenyl)ureido]-N-[4-(2-cyaniminoimidazolidin-1-yl)phenyl]valeramide.

The following compounds are obtained analogously:
(R)-2-[3-(4-chlorophenyl)ureido]-N-[4-(2-cyanimino-3-methylimidazolidin-1-yl)phenyl]valeramide;
(R)-2-[3-(4-chlorophenyl)ureido]-N-[4-(2-cyanimino-3-methylimidazolidin-1-yl)phenyl]-2-phenylacetamide;
(R)-2-[3-(4-chlorophenyl)ureido]-N-[4-(2-cyanimino-3-methylimidazolidin-1-yl)phenyl]-2-thiophen-2-ylacetamide.

EXAMPLE 5

The following compounds are obtained analogously to Example 2:
(R)-2-[3-(4-chlorophenyl)ureido]-N-[4-(2-iminopyrrolidin-1-yl)-3-methylphenyl]-2-(2-thienyl)acetamide, ESI 482;
(R)-2-[3-(4-chlorophenyl)ureido]-N-[4-(2-iminoimidazolidin-1-yl)-3-methylphenyl]-2-(2-thienyl)acetamide, trifluoroacetate, ESI 483;
(R)-2-[3-(4-chlorophenyl)ureido]-N-[4-(2-iminoimidazolidin-1-yl)-3-methylphenyl]-2-phenylacetamide, trifluoroacetate, ESI 477;
(R)-2-[3-(4-chlorophenyl)ureido]-N-[4-(2-iminoimidazolidin-1-yl)-3-methylphenyl]valeramide, trifluoroacetate, ESI 443.

EXAMPLE 6

The following compounds are obtained analogously to Example 1:
2-[N-(4-chlorophenyl)carbamoyloxy]-N-[4-(2-iminopyrrolidin-1-yl)-phenyl]-2-(2-fluorophenyl)acetamide, citrate, ESI 481;
(R)-2-[N-(4-chlorophenyl)carbamoyloxy]-N-[4-(2-iminopyrrolidin-1-yl)phenyl]-2-phenylacetamide, tartrate, ESI 463;
2-[N-(4-chlorophenyl)carbamoyloxy]-N-[4-(2-methoxyiminopiperidin-1-yl)phenyl]-2-(2-fluorophenyl)acetamide, ESI 539;
2-[N-(4-chlorophenyl)carbamoyloxy]-N-[4-(2-methoxyiminopyrrolidin-1-yl)phenyl]-2-(2-fluorophenyl)acetamide, ESI 511;
2-[N-(4-chlorophenyl)carbamoyloxy]-N-[4-(2-iminopyrrolidin-1-yl)-phenyl]-2-(2-fluorophenyl)acetamide, citrate, ESI 495;
(R)-2-[N-(4-chlorophenyl)carbamoyloxy]-N-[4-(2-iminopyrrolidin-1-yl)phenyl]-2-phenylacetamide, lactate, ESI 463.

EXAMPLE 7

The following compounds are obtained analogously to Example 3:
(R)-2-[3-(4-chloro-2-methylphenyl)ureido]-N-[4-(2-iminopyrrolidin-1-yl)phenyl]-2-(2-thienyl)acetamide, ESI 482;
(R)-2-[3-(4-chlorophenyl)ureido]-N-[4-(2-iminopiperidin-1-yl)-phenyl]-2-phenylacetamide, tartrate, ESI 476;
(S)-2-[3-(4-chlorophenyl)ureido]-N-[4-(2-iminopyrrolidin-1-yl)-phenyl]-2-phenylacetamide, D-(-)-tartrate, ESI 462;
(S)-2-[3-(4-chlorophenyl)ureido]-N-[4-(2-iminopiperidin-1-yl)-phenyl]-2-phenylacetamide, D-(-)-tartrate, ESI 476;
(R)-2-[3-(4-chlorophenyl)ureido]-N-[4-(2-iminoimidazolidin-1-yl)-phenyl]-2-(2-thienyl)acetamide, trifluoroacetate, ESI 469;
(R)-2-[3-(4-chlorophenyl)ureido]-N-[4-(2-imino-5-methyl-1,3,4-thiadiazol-3-yl)phenyl]-2-phenylacetamide, trifluoroacetate, ESI 493;
(R)-2-[3-(4-chlorophenyl)ureido]-N-[4-(2-iminoimidazolidin- 1-yl)-phenyl]-2-phenylacetamide, trifluoroacetate, ESI 463;
(R)-2-[3-(4-chlorophenyl)ureido]-N-[4-(2-cyaniminoimidazolidin-1-yl)phenyl]-2-phenylacetamide, ESI 502;
(R)-2-[3-(4-chlorophenyl)ureido]-N-[4-(2-cyaniminoimidazolidin-1-yl)phenyl]-2-(2-thienyl)acetamide, ESI 508;
(R)-2-[3-(4-chlorophenyl)ureido]-N-[4-(2-cyaniminoimidazolidin-1-yl)phenyl]valeramide, ESI 454;
(R)-2-[3-(4-chlorophenyl)ureido]-N-[4-(2-cyanimino-3-methyl-imidazolidin-1-yl)phenyl]valeramide, ESI 468;
(R)-2-[3-(4-chlorophenyl)ureido]-N-[4-(2-iminoimidazolidin-1-yl)-phenyl]valeramide, trifluoroacetate, ESI 429;
(R)-2-[3-(4-chlorophenyl)ureido]-N-[4-(2-iminopyrrolidin-1-yl)-phenyl]valeramide, trifluoroacetate, ESI 428;
2-[3-(4-chlorophenyl)ureido]-N-[4-(2-iminopyrrolidin-1-yl)phenyl]-acetamide, trifluoroacetate, ESI 387;
2-[3-(4-chlorophenyl)ureido]-N-[4-(2-cyanimino-3-methylimidazolidin-1-yl)phenyl]acetamide, trifluoroacetate, ESI 426;
2-[3-(4-chlorophenyl)ureido]-N-[4-(2-iminopyrrolidin-1-yl)-phenyl]acetamide, trifluoroacetate, ESI 426;
(R)-2-[3-(4-chlorophenyl)ureido]-N-[4-(2-iminoimidazolidin-1-yl)-phenyl]propionamide, trifluoroacetate, ESI 401;

(R)-2-[3-(4-chlorophenyl)ureido]-N-[4-(2-cyanimino-3-methylimidazolidin-1-yl)phenyl]propionamide, trifluoroacetate, ESI 440;
(R)-2-[3-(4-chlorophenyl)ureido]-N-[4-(2-iminopyrrolidin-1-yl)-phenyl]propionamide, trifluoroacetate, ESI 400;
(R)-2-[3-(4-chlorophenyl)ureido]-N-[4-(2-iminoimidazolidin-1-yl)-phenyl]-3-methylbutyramide, trifluoroacetate, ESI 429;
(R)-2-[3-(4-chlorophenyl)ureido]-N-[4-(2-cyanimino-3-methylimidazolidin-1-yl)phenyl]-3-methylbutyramide, trifluoroacetate, ESI 468;
(R)-2-[3-(4-chlorophenyl)ureido]-N-[4-(2-iminopyrrolidin-1-yl)-phenyl]-3-methylbutyramide, trifluoroacetate, ESI 428;
(R)-2-[3-(4-chlorophenyl)ureido]-N-[4-(2-iminoimidazolidin-1-yl)-phenyl]-4-methylvaleramide, trifluoroacetate, ESI 443;
(R)-2-[3-(4-chlorophenyl)ureido]-N-[4-(2-cyanimino-3-methylimidazolidin-1-yl)phenyl]-4-methylvaleramide, trifluoroacetate, ESI 482;
(R)-2-[3-(4-chlorophenyl)ureido]-N-[4-(2-iminopyrrolidin-1-yl)-phenyl]-4-methylvaleramide, trifluoroacetate, ESI 442;
2-[3-(4-chlorophenyl)ureido]-N-[4-(2-iminopyrrolidin-1-yl)phenyl]-3-methoxypropionamide, trifluoroacetate, ESI 430;
2-[3-(4-chlorophenyl)ureido]-N-[4-(2-cyaniminoimidazolidin-1-yl)-phenyl]-3-methoxypropionamide, ESI 456;
(R)-2-[3-(4-chlorophenyl)ureido]-N-[4-(2-cyaniminoimidazolidin-1-yl)phenyl]-3-(1-methyl-1H-imidazol-4-yl)propionamide, trifluoroacetate, ESI 506;
2-[3-(4-chlorophenyl)ureido]-N-[4-(5-ethyl-2-imino-1,3,4-thiadiazol-3-yl)phenyl]-3-methoxypropionamide, trifluoroacetate, ESI 475;
2-[3-(4-chlorophenyl)ureido]-N-[4-(5-aminocarbonyl-2-imino-1,3,4-thiadiazol-3-yl)phenyl]-3-methoxypropionamide, trifluoroacetate, ESI 490;
2-[3-(4-chlorophenyl)ureido]-N-[4-(5-ethoxycarbonyl-2-imino-1, 3,4-thiadiazol-3-yl)phenyl]-3-methoxypropionamide, trifluoroacetate, ESI 519;
2-[3-(4-chlorophenyl)ureido]-N-[4-(2-iminopiperidin-1-yl)phenyl]-4-methylsulfonylbutyramide.

Pharmacological Data

Affinity to Receptors

TABLE 1

| Compound No. | FXa-IC$_{50}$ [M] | TF/FVIIa-IC$_{50}$ [M] |
|---|---|---|
| "AB" | $5.8 \times 10^{-8}$ | $9.9 \times 10^{-8}$ |
| "BA" | $6.8 \times 10^{-7}$ | $4.9 \times 10^{-7}$ |
| "BB" | $2.7 \times 10^{-6}$ | $2.0 \times 10^{-6}$ |
| "AA" | $2.2 \times 10^{-7}$ | $2.9 \times 10^{-7}$ |
| "CA" | $5.4 \times 10^{-8}$ | |

The following examples relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of NaH$_2$PO$_4$.2 H$_2$O, 28.48 g of Na$_2$HPO$_4$.12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula I

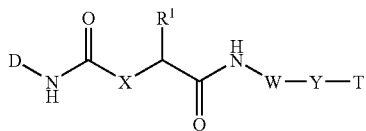

in which
D is phenyl, pyridyl or thienyl, each of which is unsubstituted or monosubstituted or polysubstituted by Hal, A, $OR^2$, $N(R^2)_2$, $NO_2$, CN, $COOR^2$ or $CON(R^2)_2$,
X is $NR^3$ or O,
$R^1$ is H, Ar, Het, cycloalkyl or A, which is optionally substituted by $OR^2$, $S(O)_mR^2$, $N(R^2)_2$, Ar, Het, cycloalkyl, CN, $COOR^2$ or $CON(R^2)_2$,
$R^2$ is H, A, —[C($R^3$)$_2$]$_n$—Ar, —[C($R^3$)$_2$]$_n$—Het, —[C($R^3$)$_2$]$_n$-cycloalkyl, —[C($R^3$)$_2$]$_n$—N($R^3$)$_2$ or —[C($R^3$)$_2$]$_n$—$OR^3$,
$R^3$ is H or A,
W is —[C($R^3$)$_2$]$_n$—,
Y is alkylene, cycloalkylene, Het-diyl or Ar-diyl,
T is a monocyclic or bicyclic saturated, unsaturated or aromatic carbocyclic or heterocyclic ring having from 1 to 4 N, O and/or S atoms which is monosubstituted or disubstituted by =S, =$NR^2$, =$NOR^2$, =$NCOR^2$=$NCOOR^2$, =$NOCOR^2$, =N—CN or =N—$NO_2$ and is optionally further monosubstituted, disubstituted or trisubstituted by Hal, A, —[C($R^3$)$_2$]$_n$—Ar, —[C($R^3$)$_2$]$_n$—Het, —[C($R^3$)$_2$]$_n$-cycloalkyl, $OR^3$, $N(R^3)_2$, $NO_2$, CN, $COOR^2$, $CON(R^2)_2$, $NR^2COA$, $NR^2CON(R^2)_2$, $NR^2SO_2A$, $COR^2$, $SO_2NR^2$ and/or $S(O)_mA$,
A is unbranched or branched alkyl having 1–10 carbon atoms, in which one or two $CH_2$ groups are optionally replaced by O or S atoms and/or by —CH=CH— groups and/or in addition 1–7 H atoms are optionally replaced by F,
Ar is phenyl, naphthyl or biphenyl, each of which is unsubstituted or monosubstituted, disubstituted or trisubstituted by Hal, A, $OR^3$, $N(R^3)_2$, $NO_2$, CN, $COOR^3$, $CON(R^3)_2$, $NR^3COA$, $NR^3CON(R^3)_2$, $NR^3SO_2A$, $COR^3$, $SO_2N(R^3)_2$, $S(O)_mA$, —[C($R^3$)$_2$]$_n$—$COOR^{2'}$ or —O—[C($R^3$)$_2$]$_o$—$COOR^{2'}$,
$R^{2'}$ is H, A, —[C($R^3$)$_2$]$_n$—Ar', —[C($R^3$)$_2$]$_n$—Het', —[C($R^3$)$_2$]$_n$-cycloalkyl, —[C($R^3$)$_2$]$_n$—N($R^3$)$_2$ or —[C($R^3$)$_2$]$_n$—$OR^3$,
$R^{2''}$ is H, A, —[C($R^3$)$_2$]$_n$—Ar' or —[C($R^3$)$_2$]$_n$-cycloalkyl, —[C($R^3$)$_2$]$_n$—N($R^3$)$_2$ or —[C($R^3$)$_2$]$_n$—$OR^3$,
Ar' is phenyl or benzyl, each of which is unsubstituted or monosubstituted or disubstituted by Hal or A,
Het is a monocyclic or bicyclic saturated, unsaturated or aromatic heterocyclic ring having from 1 to 4 N, O and/or S atoms, which is unsubstituted or monosubstituted, disubstituted or trisubstituted by carbonyl oxygen, =S, =$N(R^3)_2$, Hal, A, —[C($R^3$)$_2$]$_n$—Ar, —[C($R^3$)$_2$]$_n$—Het¹, —[C($R^3$)$_2$]$_n$-cycloalkyl, —[C($R^3$)$_2$]$_n$—$OR^{2''}$, —[C($R^3$)$_2$]$_n$—N($R^{2''}$)$_2$, $NO_2$, CN, —[C($R^3$)$_2$]$_n$—$COOR^{2''}$, —[C($R^3$)$_2$]$_n$—$CON(R^{2''})_2$, $NR^{2''}COA$, $NR^{2''}CON(R^{2''})_2$, —[C($R^3$)$_2$]$_n$—$NR^{2''}SO_2A$, $COR^{2''}$, $SO_2NR^{2'}$ and/or $S(O)_mA$,
Het¹ is a monocyclic or bicyclic saturated, unsaturated or aromatic heterocyclic ring having 1 or 2 N, O and/or S atoms, which is unsubstituted or monosubstituted or disubstituted by carbonyl oxygen, =S, =$N(R^3)_2$, Hal, A, $OR^{2''}$, $N(R^{2''})_2$, $NO_2$, CN, $COOR^{2''}$, $CON(R^{2''})_2$, $NR^{2''}COA$, $NR^{2''}CON(R^{2''})_2$, $NR^{2''}SO_2A$, $COR^{2''}$, $SO_2NR^{2''}$ and/or $S(O)_mA$,
Hal is F, Cl, Br or I,
n is 0, 1 or 2,
m is 0, 1 or 2,
o is 1, 2 or 3,
and pharmaceutically acceptable salts, solvates and stereoisomers thereof, including mixtures thereof in all ratios.

2. Compounds according to claim 1, in which
D is phenyl which is unsubstituted or monosubstituted or disubstituted by Hal, A, $OR^2$ or $COOR^2$ or is pyridyl or thienyl, each of which is unsubstituted or monosubstituted by Hal,
and pharmaceutically acceptable salts, solvates and stereoisomers thereof, including mixtures thereof in all ratios.

3. Compounds according to claim 1, in which
$R^2$ is H or alkyl having 1, 2, 3, 4, 5 or 6 carbon atoms, and pharmaceutically acceptable salts, solvates and stereoisomers thereof, including mixtures thereof in all ratios.

4. Compounds according to claim 1, in which
$R^1$ is H, phenyl or thienyl, each of which is unsubstituted or monosubstituted or disubstituted by Hal and/or A, or is alkyl having 1–6 carbon atoms, which may be substituted by thiophene, imidazole, indole, $S(O)_mR^2$, $OR^2$, cycloalkyl or phenyl, where the imidazole ring may have a substituent A,
and pharmaceutically acceptable salts, solvates and stereoisomers thereof, including mixtures thereof in all ratios.

5. Compounds according to claim 1, in which
X is NH or O,
and pharmaceutically acceptable salts, solvates and stereoisomers thereof, including mixtures thereof in all ratios.

6. Compounds according to claim 1, in which
W is $(CH_2)_n$,
and pharmaceutically acceptable salts, solvates and stereoisomers thereof, including mixtures thereof in all ratios.

7. Compounds according to claim 1, in which
Y is Ar-diyl or Het-diyl,
and pharmaceutically acceptable salts, solvates and stereoisomers thereof, including mixtures thereof in all ratios.

8. Compounds according to claim 1, in which
T is a monocyclic or bicyclic saturated, unsaturated or aromatic carbocyclic or heterocyclic ring having from 1 to 3 N, O and/or S atoms which is monosubstituted or disubstituted by =S, =$NR^2$, =$NOR^2$, =$NCOR_2$, =$NCOOR^2$, =$NOCOR^2$, =N—CN or =N—$NO_2$ and may furthermore be monosubstituted or disubstituted by Hal, A, $CONH_2$ or COOA,
and pharmaceutically acceptable salts, solvates and stereoisomers thereof, including mixtures thereof in all ratios.

9. Compounds according to claim 1, in which
T is a monocyclic or bicyclic saturated or unsaturated heterocyclic ring having 1 or 2 N and/or O atoms which is monosubstituted or disubstituted by =$NR^2$, =S, =$NOR^2$, =N—CN or =N—$NO_2$, and pharmaceutically acceptable salts, solvates and stereoisomers thereof, including mixtures thereof in all ratios.

10. Compounds according to claim 1, in which

T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted or disubstituted by $=NR^2$, $=S$, $=NOR^2$ or $=N-CN$, where the thiadiazole ring is optionally substituted by A, $CONH_2$ or COOA, A' is alkyl having 1, 2, 3, 4, 5 or 6 carbon atoms, in which 1–7 H atoms are optionally replaced by F, and pharmaceutically acceptable salts, solvates and stereoisomers thereof, including mixtures thereof in all ratios.

11. Compounds according to claim 1, in which

T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted or disubstituted by $=NR^{2b}$, $=S$, $=NOR^{2b}$ or $=N-CN$, where the thiadiazole ring is optionally substituted by A, $CONH_2$ or COOA, $R^{2b}$ is H, OH or OA', A' is alkyl having 1, 2, 3, 4, 5 or 6 carbon atoms, in which 1–7 H atoms are optionally replaced by F, and pharmaceutically acceptable salts, solvates and stereoisomers thereof, including mixtures thereof in all ratios.

12. Compounds according to claim 1, in which

T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted or disubstituted by $=NR^{2b}$, $=S$, $=NOR^{2b}$ or $=N-CN$, $R^{2b}$ is H, OH or OA", A" is methyl, ethyl, propyl, isopropyl or butyl, and pharmaceutically acceptable salts, solvates and stereoisomers thereof, including mixtures thereof in all ratios.

13. Compounds according to claim 1, in which

Ar is phenyl which is unsubstituted or monosubstituted or disubstituted by Hal, A, OA, $SO_2A$, $COOR^2$, $SO_2NH_2$ or CN, and pharmaceutically acceptable salts, solvates and stereoisomers thereof, including mixtures thereof in all ratios.

14. Compounds according to claim 1, in which

D is phenyl which is unsubstituted or monosubstituted by Hal or is pyridyl or thienyl, each of which is unsubstituted or monosubstituted by Hal, $R^1$ is H, phenyl or thienyl, each of which is unsubstituted or monosubstituted or disubstituted by Hal and/or A, or is alkyl having 1–6 carbon atoms, which is optionally substituted by thiophene, imidazole, indole, $S(O)_mR^2$, $OR^2$, cycloalkyl or phenyl, where the imidazole ring optionally has a substituent A, X is NH or O, W is absent, Y is Ar-diyl, pyridinediyl or piperidinediyl, Ar is phenyl which is unsubstituted or monosubstituted or disubstituted by Hal, A, OA, $SO_2A$, $COOR^2$, $SO_2NH_2$ or CN, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by $=NR^{2b}$, $=S$, $=NOR^{2b}$ or $=N-CN$, where the thiadiazole ring is optionally substituted by A, $CONH_2$ or COOA, $R^{2b}$ is H, OH or OA", A" is methyl, ethyl, propyl, isopropyl or butyl, and pharmaceutically acceptable salts, solvates and stereoisomers thereof, including mixtures thereof in all ratios.

15. Compounds according to claim 1, in which

D is phenyl which is unsubstituted or monosubstituted by Hal or is pyridyl or thienyl, each of which is unsubstituted or monosubstituted by Hal, $R^1$ is H, phenyl or thienyl, each of which is unsubstituted or monosubstituted or disubstituted by Hal and/or A, or is alkyl having 1–6 carbon atoms, which is optionally substituted by thiophene, imidazole, indole, $S(O)_mR^2$, $OR^2$, cycloalkyl or phenyl, where the imidazole ring optionally has a substituent A, X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by $=NR^{2b}$, $=S$, $=NOR^{2b}$ or $=N-CN$, where the thiadiazole ring is optionally substituted by A, $CONH_2$ or COOA, $R^{2b}$ is H, OH or OA", A" is methyl, ethyl, propyl, isopropyl or butyl, and pharmaceutically acceptable salts, solvates and stereoisomers thereof, including mixtures thereof in all ratios.

16. Compounds according to claim 1, in which

D is phenyl or thienyl, each of which is unsubstituted or monosubstituted by Hal, $R^1$ is H, phenyl which is unsubstituted or monosubstituted by Hal, or alkyl having 1–6 carbon atoms, X is NH or O, W is absent, Y is Ar-diyl, Ar is phenyl which is unsubstituted or monosubstituted or disubstituted by Hal or A, T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted by $=NR^{2b}$, $=S$, $=NOR^{2b}$ or $=N-CN$, $R^{2b}$ is H, OH or OA", A" is methyl, ethyl, propyl, isopropyl or butyl, and pharmaceutically acceptable salts, solvates and stereoisomers thereof, including mixtures thereof in all ratios.

17. Compounds according to claim 1, in which

D is phenyl or thienyl, each of which is unsubstituted or monosubstituted by Hal, $R^1$ is H, phenyl which is unsubstituted or monosubstituted by Hal, alkyl having 1–6 carbon atoms or Het', X is NH or O,
W is absent,
Y is Ar-diyl,
Ar is phenyl which is unsubstituted or monosubstituted or disubstituted by Hal or A,
T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl or 3-A"-imidazolidin-1-yl, each of which is monosubstituted by =$NR^{2b}$, =S, =$NOR^{2b}$ or =N—CN,
$R^{2b}$ is H, OH or OA",
A" is methyl, ethyl, propyl, isopropyl or butyl,
Het' is 2-thienyl or 2-furyl,
and pharmaceutically acceptable salts, solvates and stereoisomers thereof, including mixtures thereof in all ratios.

18. Compounds according to claim 1, in which
D is phenyl or thienyl, each of which is unsubstituted or monosubstituted by Hal,
$R^1$ is H, phenyl which is unsubstituted or monosubstituted or disubstituted by Hal and/or A, alkyl having 1–6 carbon atoms or Het', or alkyl having 1–6 carbon atoms which is optionally substituted by thiophene, imidazole, indole, $S(O)_m A"$, OA", cycloalkyl or phenyl, where the imidazole ring optionally has a substituent A",
X is NH or O,
W is absent,
Y is Ar-diyl,
Ar is phenyl which is unsubstituted or monosubstituted or disubstituted by Hal or A,
T is piperidin-1-yl, pyrrolidin-1-yl, 1H-pyridin-1-yl, morpholin-4-yl, piperazin-1-yl, 1,3-oxazolidin-3-yl, 2H-pyridazin-2-yl, azepan-1-yl, 2-azabicyclo[2.2.2]octan-2-yl, imidazolidin-1-yl, 3-A'-imidazolidin-1-yl or thiadiazolyl, each of which is monosubstituted by =$NR^{2b}$, =S, =$NOR^{2b}$ or =N—CN, where the thiadiazole ring is optionally substituted by A", $CONH_2$ or COOA",
$R^{2b}$ is H, OH or OA",
A" is methyl, ethyl, propyl, isopropyl or butyl,
Het' is 2-thienyl or 2-furyl,
and pharmaceutically acceptable salts, solvates and stereoisomers thereof, including mixtures thereof in all ratios.

19. Compounds according to claim 1 selected from the group consisting of
(R)-2-[N-(4-chlorophenyl)carbamoyloxy]-N-[4-(2-methoxyiminopiperidin-1-yl)phenyl]-2-phenylacetamide,
(R)-2-[N-(4-chlorophenyl)carbamoyloxy]-N-[4-(2-iminopiperidin-1-yl)phenyl]-2-phenylacetamide,
(R)-2-[N-(4-chlorophenyl)carbamoyloxy]-N-[4-(2-iminopiperidin-1-yl)-3-methylphenyl]-2-phenylacetamide,
(R)-2-[N-(4-chlorophenyl)carbamoyloxy]-N-[4-(2-iminopyrrolidin-1-yl)-3-methylphenyl]-2-phenylacetamide,
(R)-2-[N-(4-chlorophenyl)carbamoyloxy]-N-[4-(2-iminopiperidin-1-yl)phenyl]-2-(2-fluorophenyl)acetamide,
2-[N-(4-chlorophenyl)carbamoyloxy]-N-[4-(2-iminopiperidin-1-yl)-phenyl]-2-(2-chlorophenyl)acetamide,
(S)-2-[N-(4-chlorophenyl)carbamoyloxy]-N-[4-(2-iminopiperidin-1-yl)phenyl]-2-phenylacetamide,
2-[N-(4-chlorophenyl)carbamoyloxy]-N-[4-(2-iminopiperidin-1-yl)-phenyl]propionamide,
(R)-2-[N-(5-chloropyridin-2-yl)carbamoyloxy]-N-[4-(2-iminopiperidin-1-yl)phenyl]-2-phenylacetamide,
(R)-2-[N-(4-chlorophenyl)carbamoyloxy]-N-[4-(2-iminopyrrolidin-1-yl)phenyl]-2-phenylacetamide,
(R)-2-[N-(4-chlorophenyl)carbamoyloxy]-N-[4-(2-iminopyrrolidin-1-yl)phenyl]-2-(2-fluorophenyl)acetamide,
(R)-2-[N-(4-chlorophenyl)carbamoyloxy]-N-[4-(2-imino-2H-pyridin-1-yl)phenyl]-2-phenylacetamide,
(R)-2-[N-(5-chlorothiophen-2-yl)carbamoyloxy]-N-[4-(2-iminopiperidin-1-yl)phenyl]-2-phenylacetamide,
(R)-2-[N-(4-chlorophenyl)carbamoyloxy]-N-[4-(3-iminomorpholin-4-yl)phenyl]-2-phenylacetamide, 2-[N-(4-chlorophenyl)carbamoyloxy]-N-[4-(2-methoxyiminopiperidin-1-yl)-3-methylphenyl]-2-(2-chlorophenyl)acetamide,
(R)-2-[N-(4-chlorophenyl)carbamoyloxy]-N-[4-(2-methoxyiminopiperidin-1-yl)-3-methylphenyl]-2-phenylacetamide,
(S)-2-[N-(4-chlorophenyl)carbamoyloxy]-N-[4-(2-methoxyiminopiperidin-1-yl)-3-methylphenyl]-2-phenylacetamide,
(R)-2-[N-(4-chlorophenyl)carbamoyloxy]-N-[4-(2-methoxyiminopyrrolidin-1-yl)phenyl]-2-phenylacetamide,
(R)-2-[N-(4-chlorophenyl)carbamoyloxy]-N-[4-(2-methoxyiminopiperidin-1-yl)-3-methylphenyl]-2-(2-chlorophenyl)acetamide,
(R)-2-[N-(4-chlorophenyl)carbamoyloxy]-N-[4-(2-azabicyclo-[2.2.2]octan-3-imino-2-yl)phenyl]-2-phenylacetamide,
(R)-2-[3-(4-chlorophenyl)ureido]-N-[4-(2-iminopyrrolidin-1-yl)-3-methylphenyl]-2-phenylacetamide,
(R)-2-[3-(4-chlorophenyl)ureido]-N-[4-(2-iminopiperidin-1-yl)-3-methylphenyl]-2-phenylacetamide, hydrochloride,
(R)-2-[3-(4-chlorophenyl)ureido]-N-[4-(2-iminopiperidin-1-yl)phenyl]-2-phenylacetamide,
(S)-2-[3-(4-chlorophenyl)ureido]-N-[4-(2-iminopiperidin-1-yl)phenyl]-2-phenylacetamide,
(R)-2-[3-(4-chlorophenyl)ureido]-N-[4-(2-iminopiperidin-1-yl)-phenyl]propionamide,
(R)-2-[3-(4-chlorophenyl)ureido]-N-[4-(2-iminopyrrolidin-1-yl)phenyl]-2-phenylacetamide,
(R)-2-[3-(4-chlorophenyl)ureido]-N-[4-(2-iminopiperidin-1-yl)phenyl]-2-(2-fluorophenyl)acetamide,
(R)-2-[3-(4-chlorophenyl)ureido]-N-[4-(2-iminopiperidin-1-yl)-phenyl]valeramide,
(R)-2-[3-(4-chlorophenyl)ureido]-N-[4-(2-iminopyrrolidin-1-yl)phenyl]-2-(2-fluorophenyl)acetamide,
(R)-2-[3-(5-chlorothiophen-2-yl)ureido]-N-[4-(2-iminopiperidin-1-yl)phenyl]-2-phenylacetamide,
(S)-2-[3-(4-chlorophenyl)ureido]-N-[4-(2-methoxyiminopiperidin-1-yl)-3-methylphenyl]-2-phenylacetamide,
(R)-2-[3-(4-chlorophenyl)ureido]-N-[4-(2-methoxyiminopyrrolidin-1-yl)phenyl]-2-phenylacetamide,
(R)-2-[3-(4-chlorophenyl)ureido]-N-[4-(2-iminopyrrolidin-1-yl)phenyl]-2-thienylacetamide,
(R)-2-[3-(4-chlorophenyl)ureido]-N-[4-(2-cyaniminoimidazolidin-1-yl)phenyl]-2-phenylacetamide,
(R)-2-[3-(4-chlorophenyl)ureido]-N-[4-(2-cyaniminoimidazolidin-1-yl)phenyl]-2-(thiophen-2-yl)acetamide,
(R)-2-[3-(4-chlorophenyl)ureido]-N-[4-(2-cyaniminoimidazolidin-1-yl)phenyl]valeramide,
(R)-2-[3-(4-chlorophenyl)ureido]-N-[4-(2-cyanimino-3-methylimidazolidin-1-yl)phenyl]valeramide, (R)-2-[3-(4-chlorophenyl)ureido]-N-[4-(2-cyanimino-3-methylimidazolidin-1-yl)phenyl]-2-phenylacetamide,
(R)-2-[3-(4-chlorophenyl)ureido]-N-[4-(2-cyanimino-3-methylimidazolidin-1-yl)phenyl]-2-thiophen-2-ylacetamide,
(R)-2-[3-(4-chlorophenyl)ureido]-N-[4-(2-iminopyrrolidin-1-yl)-3-methylphenyl]-2-(2-thienyl)acetamide,
(R)-2-[3-(4-chlorophenyl)ureido]-N-[4-(2-iminoimidazolidin-1-yl)-3-methylphenyl]-2-(2-thienyl)acetamide,
(R)-2-[3-(4-chlorophenyl)ureido]-N-[4-(2-iminoimidazolidin-1-yl)-3-methylphenyl]-2-phenylacetamide,
(R)-2-[3-(4-chlorophenyl)ureido]-N-[4-(2-iminoimidazolidin-1-yl)-3-methylphenyl]valeramide,
2-[N-(4-chlorophenyl)carbamoyloxy]-N-[4-(2-iminopyrrolidin-1-yl)phenyl]-2-(2-fluorophenyl)acetamide, citrate,
(R)-2-[N-(4-chlorophenyl)carbamoyloxy]-N-[4-(2-iminopyrrolidin-1-yl)phenyl]-2-phenylacetamide, tartrate,
2-[N-(4-chlorophenyl)carbamoyloxy]-N-[4-(2-methoxyiminopiperidin-1-yl)phenyl]-2-(2-fluorophenyl)acetamide,
2-[N-(4-chlorophenyl)carbamoyloxy]-N-[4-(2-methoxyiminopyrrolidin-1-yl)phenyl]-2-(2-fluorophenyl)acetamide,
2-[N-(4-chlorophenyl)carbamoyloxy]-N-[4-(2-iminopyrrolidin-1-yl)phenyl]-2-(2-fluorophenyl)acetamide,
(R)-2-[N-(4-chlorophenyl)carbamoyloxy]-N-[4-(2-iminopyrrolidin-1-yl)phenyl]-2-phenylacetamide, lactate,
(R)-2-[3-(4-chloro2-methylphenyl)ureido]-N-[4-(2-iminopyrrolidin-1-yl)phenyl]-2-(2-thienyl)acetamide,
(R)-2-[3-(4-chlorophenyl)ureido]-N-[4-(2-iminopiperidin-1-yl)phenyl]-2-phenylacetamide,
(S)-2-[3-(4-chlorophenyl)ureido]-N-[4-(2-iminopyrrolidin-1-yl)phenyl]-2-phenylacetamide,
(S)-2-[3-(4-chlorophenyl)ureido]-N-[4-(2-iminopiperidin-1-yl)phenyl]-2-phenylacetamide,
(R)-2-[3-(4-chlorophenyl)ureido]-N-[4-(2-iminoimidazolidin-1-yl)-phenyl]-2-(2-thienyl)acetamide,
(R)-2-[3-(4-chlorophenyl)ureido]-N-[4-(2-imino-5-methyl-1,3,4-thiadiazol-3-yl)phenyl]-2-phenylacetamide,
(R)-2-[3-(4-chlorophenyl)ureido]-N-[4-(2-iminoimidazolidin-1-yl)-phenyl]-2-phenylacetamide,
(R)-2-[3-(4-chlorophenyl)ureido]-N-[4-(2-cyaniminoimidazolidin-1-yl)phenyl]-2-phenylacetamide,
(R)-2-[3-(4-chlorophenyl)ureido]-N-[4-(2-cyaniminoimidazolidin-1-yl)phenyl]-2-(2-thienyl)acetamide,
(R)-2-[3-(4-chlorophenyl)ureido]-N-[4-(2-cyaniminoimidazolidin-1-yl)phenyl]valeramide,
(R)-2-[3-(4-chlorophenyl)ureido]-N-[4-(2-cyanimino-3-methylimidazolidin-1-yl)phenyl]valeramide,
(R)-2-[3-(4-chlorophenyl)ureido]-N-[4-(2-iminoimidazolidin-1-yl)phenyl]valeramide,
(R)-2-[3-(4-chlorophenyl)ureido]-N-[4-(2-iminopyrrolidin-1-yl)-phenyl]valeramide,
2-[3-(4-chlorophenyl)ureido]-N-[4-(2-iminopyrrolidin-1-yl)-phenyl]acetamide,
2-[3-(4-chlorophenyl)ureido]-N-[4-(2-cyanimino-3-methylimidazolidin-1-yl)phenyl]acetamide,
2-[3-(4-chlorophenyl)ureido]-N-[4-(2-iminopyrrolidin-1-yl)-phenyl]acetamide,
(R)-2-[3-(4-chlorophenyl)ureido]-N-[4-(2-iminoimidazolidin-1-yl)phenyl]propionamide,
(R)-2-[3-(4-chlorophenyl)ureido]-N-[4-(2-cyanimino-3-methylimidazolidin-1-yl)phenyl]propionamide,
(R)-2-[3-(4-chlorophenyl)ureido]-N-[4-(2-iminopyrrolidin-1-yl)-phenyl]propionamide,
(R)-2-[3-(4-chlorophenyl)ureido]-N-[4-(2-iminoimidazolidin-1-yl)phenyl]-3-methylbutyramide,
(R)-2-[3-(4-chlorophenyl)ureido]-N-[4-(2-cyanimino-3-methylimidazolidin-1-yl)phenyl]-3-methylbutyramide,
(R)-2-[3-(4-chlorophenyl)ureido]-N-[4-(2-iminopyrrolidin-1-yl)phenyl]-3-methylbutyramide,
(R)-2-[3-(4-chlorophenyl)ureido]-N-[4-(2-iminoimidazolidin-1-yl)phenyl]-4-methylvaleramide,
(R)-2-[3-(4-chlorophenyl)ureido]-N-[4-(2-cyanimino-3-methylimidazolidin-1-yl)phenyl]-4-methylvaleramide,
(R)-2-[3-(4-chlorophenyl)ureido]-N-[4-(2-iminopyrrolidin-1-yl)phenyl]-4-methylvaleramide,
2-[3-(4-chlorophenyl)ureido]-N-[4-(2-iminopyrrolidin-1-yl)phenyl]-3-methoxypropionamide,
2-[3-(4-chlorophenyl)ureido]-N-[4-(2-cyaniminoimidazolidin-1-yl)phenyl]-3-methoxypropionamide,
(R)-2-[3-(4-chlorophenyl)ureido]-N-[4-(2-cyaniminoimidazolidin-1-yl)phenyl]-3-(1-methyl-1H-imidazol-4-yl)propionamide,
2-[3-(4-chlorophenyl)ureido]-N-[4-(5-ethyl-2-imino-1,3,4-thiadiazol-3-yl)phenyl]-3-methoxypropionamide,
2-[3-(4-chlorophenyl)ureido]-N-[4-(5-aminocarbonyl-2-imino-1,3,4-thiadiazol-3-yl)phenyl]-3-methoxypropionamide,
2-[3-(4-chlorophenyl)ureido]-N-[4-(5-ethoxycarbonyl-2-imino-1,3,4-thiadiazol-3-yl)phenyl]-3-methoxypropionamide,
2-[3-(4-chlorophenyl)ureido]-N-[4-(2-iminopiperidin-1-yl)phenyl]-4-methylsulfonylbutyramide,
and pharmaceutically acceptable salts, solvates and stereoisomers thereof, including mixtures thereof in all ratios.

20. Process for the preparation of compounds of the formula I according to claim 1 and pharmaceutically acceptable salts, solvates and stereoisomers thereof, which comprises:

a) reacting a compound of the formula II

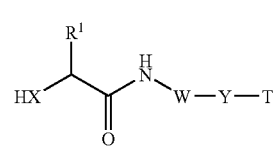

II in which

R$^1$, W, Y and T are as defined in claim 1, with a compound of the formula III

III in which

D is as defined in claim 1, or b) reacting a compound of the formula IV

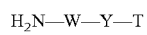

IV which W, Y and T are as defined in claim 1, with a compound of the formula V

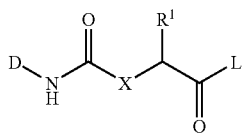

in which
- L is Cl, Br, I or a free or reactively functionally modified OH group, and
- R¹, X and D are as defined in claim 1, and/or c) converting a radical T in a compound of the formula I into another radical T and/or d) converting a base or acid of the formula I into one of its salts, or solvates.

21. Compounds of the formula I according to claim 1 wherein the compounds have activity as inhibitors of coagulation factor Xa.

22. Compounds of the formula I according to claim 1 wherein the compounds have activity as inhibitors of coagulation factor VIIa.

23. A medicament composition comprising at least one compound of the formula I according to claim 1 and/or a pharmaceutically acceptable salt, solvate or stereoisomers thereof, including mixtures thereof in all ratios, and at least one excipient and/or adjuvant.

24. A medicament composition comprising at least one compound of the formula I according to claim 1 and/or a pharmaceutically acceptable salt, solvate and stereoisomer thereof, including mixtures thereof in all ratios, and at least one further medicament active ingredient.

25. A method for the preparation of a medicament, which comprises bringing a compound according to claim 1 and/or a pharmaceutically acceptable salt, prodrug, solvate or steroisomer thereof, including mixtures thereof in all ratios, into a pharmaceutically administrative form.

26. A kit consisting of multiple separate packs of
   (a) an effective amount of a compound of the formula I according to claim 1 and/or a pharmaceutically acceptable salt, solvate or stereoisomer thereof, including mixtures thereof in all ratios, and
   (b) an effective amount of a further medicament active ingredient.

27. A method for the prepatation of a medicament, which comprises bringing a compound according to claim 1 and/or a pharmaceutically acceptable salt, prodrug, solvate or stereoisomer thereof, including mixtures thereof in all ratios, into a pharmaceutically administrable form in combination with at least one further medicament active ingredient.

* * * * *

UNITED STATES PATENT AND TRADEMARK OFFICE
CERTIFICATE OF CORRECTION

PATENT NO. : 7,183,277 B2
APPLICATION NO. : 10/512478
DATED : February 27, 2007
INVENTOR(S) : Dieter Dorsch Page 1 of 1

It is certified that error appears in the above-identified patent and that said Letters Patent is hereby corrected as shown below:

Column 29, line 20, reads " $-[C(R^3)_{2]n}-Ar$," should read -- $-[C(R^3)_2]_n-Ar$ --

Column 29, line 30, reads "=$NCOR^2$=$NCOOR^2$" should read -- =$NCOR^2$,=$NCOOR^2$ --

Column 30, line 56, reads "=$NCOR_2$," should read -- =$NCOR^2$ --

Column 35, line 29, reads "(4-chloro2-methylphenyl)" should read
-- (4-chloro-2-methylphenyl) --

Column 37, line 28, reads "stereoisomers" should read -- stereoisomer --

Column 38, line 5, reads "solvate and stereoisomer" should read -- solvate or stereoisomer --

Column 38, line 8, reads "medicament, which" should read -- medicament which --

Column 38, line 10, delete "prodrug"

Column 38, line 10 and 11, reads "or steroisomer" should read -- or stereoisomer --

Column 38, line 12, reads "administrative form" should read -- administerable form --

Column 38, line 21, reads "prepatation of a medicament, which" should read
-- preparation of a medicament which --

Column 38, line 23, delete "prodrug"

Signed and Sealed this

Twenty-third Day of October, 2007

JON W. DUDAS
*Director of the United States Patent and Trademark Office*